United States Patent
Parker et al.

(10) Patent No.: US 9,381,356 B2
(45) Date of Patent: Jul. 5, 2016

(54) METHOD AND APPARATUS FOR CONTROLLING A NEURAL STIMULUS

(75) Inventors: John Louis Parker, Artarmon (AU); James Hamilton Laird, Atarmon (AU); Dean Michael Karantonis, Artarmon (AU); Milan Obradovic, Artarmon (AU); Robert Bruce Gorman, Artarmon (AU)

(73) Assignee: Saluda Medical Pty Ltd., Artarmon (AU)

( * ) Notice: Subject to any disclaimer, the term of this patent is extended or adjusted under 35 U.S.C. 154(b) by 119 days.

(21) Appl. No.: 14/117,149

(22) PCT Filed: May 11, 2012

(86) PCT No.: PCT/AT2012/000516
§ 371 (c)(1),
(2), (4) Date: Nov. 12, 2013

(87) PCT Pub. No.: WO2012/155188
PCT Pub. Date: Nov. 22, 2012

(65) Prior Publication Data
US 2014/0236257 A1    Aug. 21, 2014

(30) Foreign Application Priority Data

May 13, 2011 (AU) ................................ 2011901817
May 13, 2011 (AU) ................................ 2011901821
May 13, 2011 (AU) ................................ 2011901827
May 13, 2011 (AU) ................................ 2011901829

(51) Int. Cl.
*A61N 1/00* (2006.01)
*A61N 1/36* (2006.01)
(Continued)

(52) U.S. Cl.
CPC ........ *A61N 1/36071* (2013.01); *A61B 5/04001* (2013.01); *A61B 5/407* (2013.01);
(Continued)

(58) Field of Classification Search
CPC ............ A61N 1/36071; A61N 1/3615; A61N 1/36139; A61N 1/0551; A61B 5/04001; A61B 5/4836; A61B 5/407
See application file for complete search history.

(56) References Cited

U.S. PATENT DOCUMENTS 3,817,254 A    6/1974  Maurer
4,418,695 A    12/1983 Buffet
(Continued)

FOREIGN PATENT DOCUMENTS

EP    0219084        4/1987
EP    2243510 A2    10/2010
(Continued)

OTHER PUBLICATIONS

Extended European Search Report for EP Application 12785483.4, completed Sep 16, 2014, 7 pgs.
(Continued)

*Primary Examiner* — Mallika D Fairchild
(74) *Attorney, Agent, or Firm* — KPPB LLP

(57) ABSTRACT

An implantable device applies and controls a neural stimulus. The device has a plurality of electrodes, and a stimulus source for providing a stimulus to be delivered from the electrodes to a neural pathway in order to evoke an action potential on the neural pathway, such as the spinal cord. A control unit controls application of a neural stimulus as defined by a set of parameter values and measures via measurement circuitry an evoked neural compound action potential response. The control unit determines from the measured evoked response a feedback variable, and compares it to a therapy map. The therapy map defines a therapeutic relationship of control variable to feedback variable. One or more of the stimulus parameter values are altered to effect the required change in the control variable. This process is performed iteratively to improve alignment of the feedback variable with the therapy map over time.

18 Claims, 15 Drawing Sheets

(51) Int. Cl.
*A61B 5/04* (2006.01)
*A61B 5/00* (2006.01)
*A61N 1/05* (2006.01)

(52) U.S. Cl.
CPC ............ *A61B 5/4041* (2013.01); *A61B 5/4824* (2013.01); *A61B 5/4836* (2013.01); *A61N 1/3615* (2013.01); *A61N 1/36139* (2013.01); *A61B 5/4821* (2013.01); *A61N 1/0551* (2013.01)

(56) References Cited

U.S. PATENT DOCUMENTS

| | | | |
|---|---|---|---|
| 4,474,186 | A | 10/1984 | Ledley et al. |
| 4,807,643 | A | 2/1989 | Rosier |
| 5,215,100 | A | 6/1993 | Spitz |
| 5,497,781 | A | 3/1996 | Chen et al. |
| 5,702,429 | A | 12/1997 | King et al. |
| 5,758,651 | A | 6/1998 | Nygard et al. |
| 5,792,212 | A | 8/1998 | Weijand et al. |
| 5,814,092 | A | 9/1998 | King |
| 5,913,882 | A | 6/1999 | King |
| 6,027,456 | A | 2/2000 | Feler et al. |
| 6,066,163 | A | 5/2000 | John |
| 6,212,431 | B1 | 4/2001 | Hahn et al. |
| 6,473,649 | B1 | 10/2002 | Gryzwa et al. |
| 6,493,576 | B1 | 12/2002 | Dankwart-Eder |
| 7,089,059 | B1 | 8/2006 | Pless |
| 7,171,261 | B1 | 1/2007 | Litvak et al. |
| 7,450,992 | B1 | 11/2008 | Cameron |
| 7,742,810 | B2 | 6/2010 | Moffitt |
| 9,155,892 | B2 | 10/2015 | Parker et al. |
| 2003/0045909 | A1 | 3/2003 | Gross et al. |
| 2003/0139781 | A1 | 7/2003 | Bradley et al. |
| 2003/0195580 | A1 | 10/2003 | Bradley et al. |
| 2004/0088017 | A1 | 5/2004 | Sharma et al. |
| 2004/0122482 | A1 | 6/2004 | Tung et al. |
| 2004/0158298 | A1* | 8/2004 | Gliner .................. A61N 1/0531 607/48 |
| 2004/0254494 | A1 | 12/2004 | Spokoyny et al. |
| 2005/0010265 | A1 | 1/2005 | Baru Fassio |
| 2005/0065427 | A1 | 3/2005 | Magill |
| 2005/0209655 | A1 | 9/2005 | Bradley et al. |
| 2006/0020291 | A1 | 1/2006 | Gozani |
| 2006/0135998 | A1 | 6/2006 | Libbus et al. |
| 2006/0195159 | A1 | 8/2006 | Bradley et al. |
| 2006/0212089 | A1 | 9/2006 | Tass |
| 2006/0217782 | A1 | 9/2006 | Boveja et al. |
| 2007/0100378 | A1 | 5/2007 | Maschino |
| 2007/0208394 | A1 | 9/2007 | King et al. |
| 2007/0225767 | A1 | 9/2007 | Daly |
| 2007/0244410 | A1 | 10/2007 | Fridman |
| 2008/0051647 | A1 | 2/2008 | Wu et al. |
| 2008/0183076 | A1 | 7/2008 | Witte |
| 2008/0234780 | A1 | 9/2008 | Smith et al. |
| 2008/0300655 | A1 | 12/2008 | Cholette et al. |
| 2009/0033486 | A1 | 2/2009 | Costantino et al. |
| 2009/0157155 | A1 | 6/2009 | Bradley |
| 2009/0299214 | A1 | 12/2009 | Wu et al. |
| 2010/0010388 | A1 | 1/2010 | Panken et al. |
| 2010/0106231 | A1 | 4/2010 | Torgerson |
| 2010/0125313 | A1 | 5/2010 | Lee et al. |
| 2010/0125314 | A1 | 5/2010 | Bradley et al. |
| 2010/0191307 | A1 | 7/2010 | Fang et al. |
| 2010/0249643 | A1 | 9/2010 | Gozani |
| 2010/0280570 | A1 | 11/2010 | Sturm et al. |
| 2010/0331604 | A1 | 12/2010 | Okamoto et al. |
| 2010/0331926 | A1 | 12/2010 | Lee et al. |
| 2011/0021943 | A1 | 1/2011 | Lacour et al. |
| 2011/0224749 | A1 | 9/2011 | Ben-David et al. |
| 2014/0194771 | A1 | 7/2014 | Parker et al. |
| 2014/0194772 | A1 | 7/2014 | Single et al. |
| 2014/0236042 | A1 | 8/2014 | Parker et al. |
| 2014/0243931 | A1 | 8/2014 | Parker et al. |
| 2015/0164354 | A1 | 6/2015 | Parker et al. |
| 2015/0374999 | A1 | 12/2015 | Parker |

FOREIGN PATENT DOCUMENTS

| | | |
|---|---|---|
| WO | 8303191 A | 9/1983 |
| WO | 9612383 A1 | 4/1996 |
| WO | 0238031 | 5/2002 |
| WO | 03043690 | 5/2003 |
| WO | 03103484 | 12/2003 |
| WO | 2004021885 A1 | 3/2004 |
| WO | 2007064936 A1 | 6/2007 |
| WO | 2009130515 A2 | 10/2009 |
| WO | 2009146427 A1 | 12/2009 |
| WO | 2010138915 A1 | 12/2010 |
| WO | 2011159545 A2 | 12/2011 |
| WO | 2012155183 A1 | 11/2012 |
| WO | 2012155188 A1 | 11/2012 |
| WO | 2013063111 A1 | 5/2013 |

OTHER PUBLICATIONS

Kent et al., "Instrumentation to Record Evoked Potentials for Closed-Loop Control of Deep Brain Stimulation", Conf. Proc. IEEE Eng. Med Biol. Sol, Aug. 2012, 10 pgs.
European Search Report for European Application 12785619.3, Search Completed Oct. 13, 2014, Mailed Oct. 23, 2014, 7 pgs.
International Search Report for International Application No. PCT/AU2012/000511, International Filing Date May 11, 2012, Search Completed May 17, 2012, Mailed May 18, 2012, 4 pgs.
International Search Report for International Application No. PCT/AU2012/000512, International Filing Date May 11, 2012, Search Completed Jul. 10, 2012, Mailed Jul. 11, 2012, 4 pgs.
International Search Report for International Application No. PCT/AU2012/000513, International Filing Date May 11, 2012, Search Completed May 29, 2012, Mailed May 30, 2012, 5 pgs.
International Search Report for International Application No. PCT/AU2012/000515, International Filing Date May 11, 2012, Search Completed May 21, 2012, Mailed Jun. 4, 2012, 5 pgs.
International Search Report for International Application No. PCT/AU2012/000516, International Filing Date May 11, 2012, Search Completed Jul. 11, 2012, Mailed Jul. 12, 2012, 8 pgs.
International Search Report for International Application No. PCT/AU2012/000517, International Filing Date May 11, 2012, Search Completed Jun. 4, 2012, Mailed Jun. 6, 2012, 3 pgs.
International Search Report for International Application No. PCT/AU2012/000518, International Filing Date May 11, 2012, Search Completed Jun. 8, 2012, Mailed Jun. 12, 2012, 4 pgs.
Written Opinion for International Application No. PCT/AU2012/000511, International Filing Date May 11, 2012, Search Completed May 17, 2012, Mailed May 18, 2012, 5 pgs.
Written Opinion for International Application No. PCT/AU2012/000512, International Filing Date May 11, 2012, Search Completed Jul. 10, 2012, Mailed Jul. 11, 2012, 7 pgs.
Written Opinion for International Application No. PCT/AU2012/000513, International Filing Date May 11, 2012, Search Completed May 29, 2012, Mailed May 30, 2012, 7 pgs.
Written Opinion for International Application No. PCT/AU2012/000515, International Filing Date May 11, 2012, Search Completed May 21, 2012, Mailed Jun. 4, 2012, 4 pgs.
Written Opinion for International Application No. PCT/AU2012/000516, International Filing Date May 11, 2012, Search Completed Jul. 11, 2012, Mailed Jul. 12, 2012, 8 pgs.
Written Opinion for International Application No. PCT/AU2012/000517, International Filing Date May 11, 2012, Search Completed Jun. 4, 2012, Mailed Jun. 6, 2012, 5 pgs.
Written Opinion for International Application No. PCT/AU2012/000518, International Filing Date May 11, 2012, Search Completed Jun. 8, 2012, Mailed Jun. 12, 2012, 10 pgs.
European Search Report for European Application 12785669.8, Search Completed Sep. 22, 2014, Mailed Sep. 29, 2014, 5 pgs.
International Search Report for Australian Application 2011901829, Search Completed Feb. 6, 2012, Mailed Feb. 7, 2012, 3pgs.

(56) References Cited

OTHER PUBLICATIONS

Andreassen, S. et al., "Muscle Fibre Conduction Velocity in Motor Units of the Human Anterior Tibial Muscle: a New Size Principle Parameter", J. Physiol. (1987), 391, pp. 561-571.

Blum, A. R., "An Electronic System for Extracelluar Neural Stimulation and Recording", Dissertation, Georgia Institute of Technology, Aug. 2007, Retrieved from http://smartech.gatech.edu/handle/1853/16192 on Jan. 30, 2012.

Dawson, G. D., "The relative excitability and conduction velocity of sensory and motor nerve fibres in man", Journal of Physiology, 1956, vol. 131(2), pp. 436-451. Figs. 1-5; Table 1; p. 437 "Methods"; pp. 438-447 "Results."

Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL. p. 324 section 'Paraesthesia Coverage by Dermatome,' p. 326 section 'Total Paraesthesia Coverage' and Figures 1 and 6-10.

Dillier, N et al., "Measurement of the electrically evoked compound action potential via a neural response telemetry system", Ann. Otol. Rhinol. Laryngol. 111 (May 2002), No. 5, pp. 407-414. Abstract & Figures 2-3, 407-414.

Fagius, J. et al., "Sympathetic Reflex Latencies and Conduction Velocities in Normal Man", Journal of Neurological Sciences, 1980. vol. 47, pp. 433-448.

Goodall, E. V., "Modeling Study of Activation and Propagation delays During Stimulation of Peripheral Nerve Fibres with a Tripolar Cuff Electrode", IEEE Trans.Rehab.Eng. V. 3, pp. 272-282.

Harper, A. A., "Conduction Velocity is Related to Morphological Cell Type in Rat Dorsal Root Ganglion Neurones", J. Physiol. (1985), 359, pp. 31-46.

Mahnam, A et al., "Measurement of the current-distance relationship using a novel refractory interaction technique", J. Neural Eng. 6 (2009), pp. 036005 (published May 20, 2009) Abstract, Sec. 2.2 & Figure 2b, 036005.

Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.

McGill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.

Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.

Parker, J. L., "Compound Action Potentials Recorded in the Human Spinal Cord During Neurostimulation for Pain Relief", Pain, vol. 153, 2012, pp. 593-601.

Roy, S. H., "Effects of Electrode Location on Myoelectric Conduction Velocity and Median Frequency Estimates", J. Appl. Physiol. 61 (4), 1986, pp. 1510-1517.

Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.

Yearwood, T. L., "Pulse Width Programming in Spinal Cord Stimulation: a Clinical Study", Pain Physician. 2010. vol. 13, pp. 321-335.

Orstavik, Kristin et al., "Pathological C-fibres in patients with a chronic painful condition", Brain (2003), 126, 567-578.

Borg et al., Conduction velocity and refractory period of single motor nerve fibres in antecedent poliomyelitis, Borg et al. 'Conduction velocity and refractory period of single motor nerve fibers in antecedent poliomyelitis' 1987, Dec. 9, 2015, 5 pgs.

Yuan, S. et al., "Recording monophasic action potentials using a platinum-electrode ablation catheter", Europace. Oct. 2000; 2(4):312-9; Abstract.

* cited by examiner

METHOD AND APPARATUS FOR CONTROLLING A NEURAL STIMULUS

CROSS-REFERENCE TO RELATED APPLICATIONS

This application claims the benefit of Australian Provisional Patent Application No. 2011901829 filed 13 May 2011, Australian Provisional Patent Application No. 2011901817 filed 13 May 2011, Australian Provisional Patent Application No. 2011901821 filed 13 May 2011 and Australian Provisional Patent Application No. 2011901827 filed 13 May 2011, each of which are incorporated herein by reference.

TECHNICAL FIELD

The present invention relates to controlling a neural response to a stimulus, and in particular relates to measurement of a compound action potential by using one or more electrodes implanted proximal to the neural pathway, in order to provide feedback to control subsequently applied stimuli.

BACKGROUND OF THE INVENTION

There are a range of situations in which it is desirable to apply neural stimuli in order to give rise to a compound action potential (CAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at 100 Hz.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin, and are thickly myelinated mechanoreceptors that respond to non-noxious stimuli. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1,P1, then a negative peak N1, followed by a second positive peak P2. This is caused by the region of activation passing the recording electrode as the action potentials propagate along the individual fibres. An observed CAP signal will typically have a maximum amplitude in the range of microvolts, whereas a stimulus applied to evoke the CAP is typically several volts.

For effective and comfortable operation, it is necessary to maintain stimuli amplitude or delivered charge above a recruitment threshold, below which a stimulus will fail to recruit any neural response. It is also necessary to apply stimuli which are below a comfort threshold, above which uncomfortable or painful percepts arise due to increasing recruitment of Aδ fibres which are thinly myelinated sensory nerve fibres associated with acute pain, cold and pressure sensation. In almost all neuromodulation applications, a single class of fibre response is desired, but the stimulus waveforms employed can recruit other classes of fibres which cause unwanted side effects, such as muscle contraction if motor fibres are recruited. The task of maintaining appropriate stimulus amplitude is made more difficult by electrode migration and/or postural changes of the implant recipient, either of which can significantly alter the neural recruitment arising from a given stimulus, depending on whether the stimulus is applied before or after the change in electrode position or user posture. Postural changes alone can cause a comfortable and effective stimulus regime to become either ineffectual or painful.

A control problem, facing neuromodulation systems of all types, is achieving neural recruitment at a sufficient level required for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the lifetime of the device.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides an automated method of controlling a neural stimulus, the method comprising:
  applying the neural stimulus to a neural pathway in order to give rise to an evoked action potential on the neural pathway, the stimulus being applied as defined by a set of parameter values;
  measuring a neural compound action potential response evoked by the stimulus and deriving from the measured evoked response a feedback variable;
  comparing the feedback variable to a therapy map, the therapy map defining a therapeutic relationship of control variable to feedback variable, and determining from the therapy map a required change in the control variable in order to improve alignment of the feedback variable with the therapy map;
  altering one or more of the stimulus parameter values to effect the required change in the control variable; and
  iteratively performing the applying, measuring, comparing and altering, in order to improve alignment of the feedback variable with the therapy map over time.

According to a second aspect the present invention provides an implantable device for controllably applying a neural stimulus, the device comprising:
  a plurality of electrodes including one or more nominal stimulus electrodes and one or more nominal sense electrodes;
  a stimulus source for providing a stimulus to be delivered from the one or more stimulus electrodes to a neural pathway in order to give rise to an evoked action potential on the neural pathway;
  measurement circuitry for recording a neural compound action potential signal sensed at the one or more sense electrodes; and
  a control unit configured to:
    control application of a neural stimulus as defined by a set of parameter values;
    measure via the measurement circuitry a neural compound action potential response evoked by the stimulus;
    determine from the measured evoked response a feedback variable;
    compare the feedback variable to a therapy map, the therapy map defining a therapeutic relationship of control variable to feedback variable;
    alter one or more of the stimulus parameter values to effect the required change in the control variable, and
    iteratively perform the applying, measuring, comparing and altering, in order to improve alignment of the feedback variable with the therapy map over time.

In preferred embodiments the therapy map defines the therapeutic relationship of control variable to feedback variable in a manner which is adaptive in response to changed recruitment sensitivity and/or measurement sensitivity, for example as may result from a changed array-to-nerve distance d, neural adaptation, or disease. For example where the feedback variable is a type of measure of evoked response strength, and the control variable is a type of stimulus intensity, the therapeutic relationship preferably represents a locus or curve defining the desired output measure of evoked response strength for a given input stimulus intensity, with the desired output measure of evoked response strength being defined in a manner which varies for varying stimulus intensity. The therapy map is preferably fitted to the individual implant recipient, and the locus or curve reflecting the therapeutic relationship may for example be a continuous curve, such as a monotonic decreasing curve. Alternatively the therapeutic relationship may define a stepped locus whereby bands of differing stimulus intensity are associated with distinct desired measures of evoked response strength. For example, the therapeutic relationship may define a stepped decreasing locus whereby bands of higher stimulus intensity are associated with a lower desired measure of evoked response strength than bands of lower stimulus intensity. To avoid a high number of transitions between adjacent bands of stimulus intensity, a hysteresis is preferably effected by way of partially overlapping stimulus intensity bands.

Fitting of the therapy map to an individual may be effected by a clinical fitting process under the control of a clinician. Alternatively the therapy map may be partly or wholly defined in an automated manner based on one or more of: user control inputs for preferred stimulus intensity; automated determinations of an electrode array-to-nerve distance d, and/or automated estimations of a stimulus threshold and comfort level for a given d.

The feedback variable could be any one of: an amplitude; an energy; a power; an integral; a signal strength; or a derivative, of any one of: the whole evoked compound action potential; the fast neural response for example in the measurement window 0-2 ms after stimulus; the slow neural response for example in the measurement window 2-6 ms after stimulus; or of a filtered version of the response. The feedback variable could in some embodiments be an average of any such variable determined over multiple stimulus/measurement cycles. The feedback variable may in some embodiments be the zero intercept, or the slope, of a linear portion of the response of $A\beta$ amplitude to varying stimulus current. In some embodiments the feedback variable may be derived from more than one of the preceding measures.

The control variable could be one or more of the total stimulus charge, stimulus current, pulse amplitude, phase duration, interphase gap duration, pulse shape, repetition rate, electrode selection and electrode combination.

Preferred embodiments provide a controlled slew rate, whereby a rate of change of the control variable is limited in order to avoid inappropriate user percepts to sudden step changes. Some embodiments preferably provide differential slew rates, whereby a rate of change of the control variable in response to a detected overstimulation condition is more rapid than a rate of change of the control variable in response to a detected understimulation condition. Such embodiments recognise that overstimulation is generally significantly more uncomfortable for the user than understimulation, so that overstimulation conditions as may arise due to postural changes should be more rapidly addressed.

In preferred embodiments, the stimulus parameters are refined on an ongoing basis in order to adaptively control the stimuli in response to postural changes of the user. In such embodiments, the parameter search space may be reassessed on a regular basis, for example once a second. Alternatively the parameter search space may be reassessed only in response to a trigger, such as a signal from an accelerometer which has detected patient movement, thereby avoiding excessive power consumption in monitoring the feedback variable at times when the patient is not moving.

In some embodiments of the invention, the feedback variable may comprise a measure of neural fibre conduction velocity. In such embodiments, the measured neural fibre conduction velocity may be used to determine selectivity of recruitment of a target fibre class, for comparison to a desired fibre class recruitment ratio or range as defined by the desired response. For example for pain suppression the desired response may be defined as requiring high selectivity of Aβ fibres.

Additionally or alternatively, the feedback variable may comprise a measure of neural response amplitude. In such embodiments, the parameter search space may be explored by iteratively applying stimuli and measuring neural responses in order to identify a "perception" threshold for stimulus current, below which no evoked response arises from stimulus. Additionally or alternatively, such embodiments may explore the parameter search space in order to identify a "maximum" or "comfort" threshold at a current level above which a slow response first starts to arise, by assessing the neural response amplitude at an expected time of occurrence of any slow response, such as about 3-4 ms after stimulation.

In embodiments where the feedback variable comprises a measure of neural response amplitude, the control variable and stimulus parameters may be refined on an ongoing basis in order to adaptively control the stimuli in response to postural changes of the user so as to maintain the evoked response amplitude at a fixed point above the perception threshold as defined by the therapy map. Such embodiments may thus enable a controlled level of neural recruitment even during user postural changes so as to conform to the therapy map, and may also be of benefit in avoiding misalignment of induced paraesthesia from a preferred location. To maximally align induced paraesthesia with a preferred location, the therapy map may include or be derived from a body map setting out the location of effects of stimuli when applied by each electrode of an electrode array. The body map may be predefined and based on patient feedback to clinical trial stimuli, or may be subject to revision during ongoing use for example by way of user input upon a remote control of the implant. The body percept map thus may contribute to definition of the therapy map.

In embodiments where the feedback variable comprises a measure of neural response amplitude, the control variable and stimulus parameters may be refined on an ongoing basis in order to maintain stimuli at a sub-threshold level, for example as may be intended for non-paraesthesia therapeutic use.

In some embodiments, the feedback variable may comprise measures of variations of an amplitude of a fast neural response in response to varied stimulus current. In such embodiments, a comfort level threshold may be defined relative to an inflection point marking decelerating growth of the fast response amplitude in response to increasing stimulus current. Such embodiments recognise that deceleration in the growth of the fast response amplitude in response to increasing stimulus current generally reflects where further recruitment starts to fall and undesirable side effects begin such as onset or increase of a slow neural response.

In some embodiments, where the feedback variable comprises measures of variations of an amplitude of a fast neural response in response to varied stimulus current, the stimulus may be maintained within a linear range of the neural recruitment vs. current curve, and an electrode-to-fibre distance d may be estimated. An estimate for d may be obtained by measuring the amplitude ($R_{e1p1}$, $R_{e5p1}$) of the neural response as measured at two spaced apart sense electrodes (denoted e1 and e5) for a first stimulus, and measuring the amplitude ($R_{e1p2}$, $R_{e5p2}$) of the neural response at the two sense electrodes for the same stimulus after a change in d. This embodiment recognises that despite a scaling factor $S_s$ due to changed measurement sensitivity with d, these measurements permit the change in recruitment scaling factor $A_s$ in response to d to be calculated as:

$$(R_{e1p2}/R_{e1p1})-(R_{e5p2}/R_{e5p1})=A_s$$

Additionally or alternatively, the electrode to fibre distance d may in some embodiments be estimated by obtaining neural response amplitude measurements in response to at least two stimuli of differing current level for constant d, the stimuli being substantially within a linear range of the neural recruitment vs. current curve. Taking a linear extrapolation of the amplitude measurements to the x-axis (i.e. the point of zero neural response) provides an estimate of the stimulus current threshold, from which an estimate of d can be produced.

In embodiments obtaining an estimate of the electrode to fibre distance d, this estimate may be used to influence the control variable and stimulus parameters and/or to appropriately scale measured neural responses to compensate for altered measurement sensitivity, in order to maintain constant or controlled neural recruitment as defined by the therapy map.

In some embodiments of the invention, the feedback variable may comprise a measure of dispersion of the response relative to distance from the stimulus site. In such embodiments, changes in dispersion may be used as indication of changes in electrode-to-fibre distance d, wherein increased dispersion correlates to increased electrode-to-fibre distance d.

In some embodiments of the invention, the feedback variable may comprise a measure of fast neural response peak position relative to stimulus. In some embodiments of the invention, the feedback variable may comprise a measure of the fast neural response $P_1$ peak width. In such embodiments, the electrode-to-fibre distance d, and/or the neural recruitment efficacy, may be estimated by reference to peak position and/or peak width of the fast neural response, with a faster narrower peak reflecting greater recruitment and potentially a movement of the electrode towards the fibre.

In some embodiments of the invention, the feedback variable may comprise a measure of spectral characteristics of the evoked response. In such embodiments, the electrode-to-fibre distance d may be determined by reference to the spectral characteristics, recognising that a transfer function of an action potential along a nerve fibre, and laterally to a sense electrode, depends on d. For example, changes in d may be detected and estimated by selecting two different frequencies which are prominent in the spectrum of the CAP, and examining the ratio between the two frequencies over time.

According to another aspect the present invention provides a computer program product comprising computer program code means to make a computer execute a procedure for automated control of a neural stimulus, the computer program product comprising computer program code means for carrying out the method of the first aspect.

BRIEF DESCRIPTION OF THE DRAWINGS

An example of the invention will now be described with reference to the accompanying drawings, in which:

FIG. 21b illustrates results of implementation of the therapy map of FIG. 21a;

DESCRIPTION OF THE PREFERRED EMBODIMENTS

Figure 1:
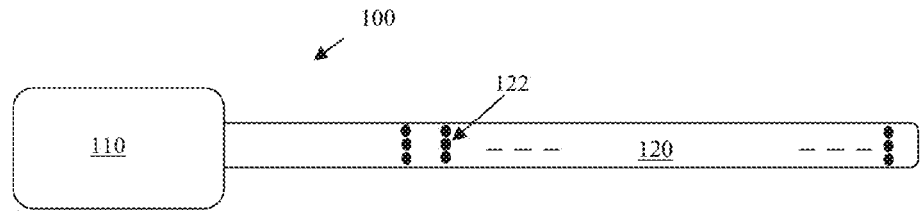
FIG. 1 illustrates an implantable device suitable for implementing the present invention.

FIG. 1 illustrates an implantable device 100 suitable for implementing the present invention. Device 100 comprises an implanted control unit 110, which controls application of neural stimuli, and controls a measurement process for obtaining a measurement of a neural response evoked by the stimuli from each of a plurality of electrodes. The control unit 110 includes a storage memory (or other storage device(s), not shown) for storing a lookup table that contains data defining the therapy map. Device 100 further comprises an electrode array 120 consisting of a three by eight array of electrodes 122, each of which may be selectively used as either the stimulus electrode or sense electrode, or both.

The evoked CAP measurements in this embodiment are made by use of the neural response measurement techniques set out in the Australian provisional patent application No. 2011901817 in the name of National ICT Australia Ltd entitled "Method and apparatus for measurement of neural response" from which the present application claims priority.

Figure 2:
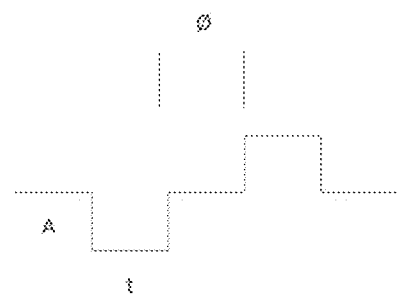
FIG. 2 is a schematic of a typical biphasic charged-balanced stimulus pulse.

Improvements in efficiency and recruitment selectivity are highly desirable. There have been two major types of stimulus waveforms used to generate propagating action potentials: voltage control and current control. Current control pulses are normally biphasic—current is passed from one electrode to another in the system, and then reversed. A typical biphasic charge-balanced stimulus pulse has an amplitude (A) and width (t) with an interphase gap φ, as shown in FIG. 2. Such a pulse applied to the spinal cord produces an evoked response. The strength of the evoked response is related to the neural recruitment, and the shape of the evoked response is related to the distribution of fibre types being recruited. Considering the parameters A, t, φ, it is possible to adjust these parameters in a systematic manner so as to obtain a desired evoked response output.

Figure 5:
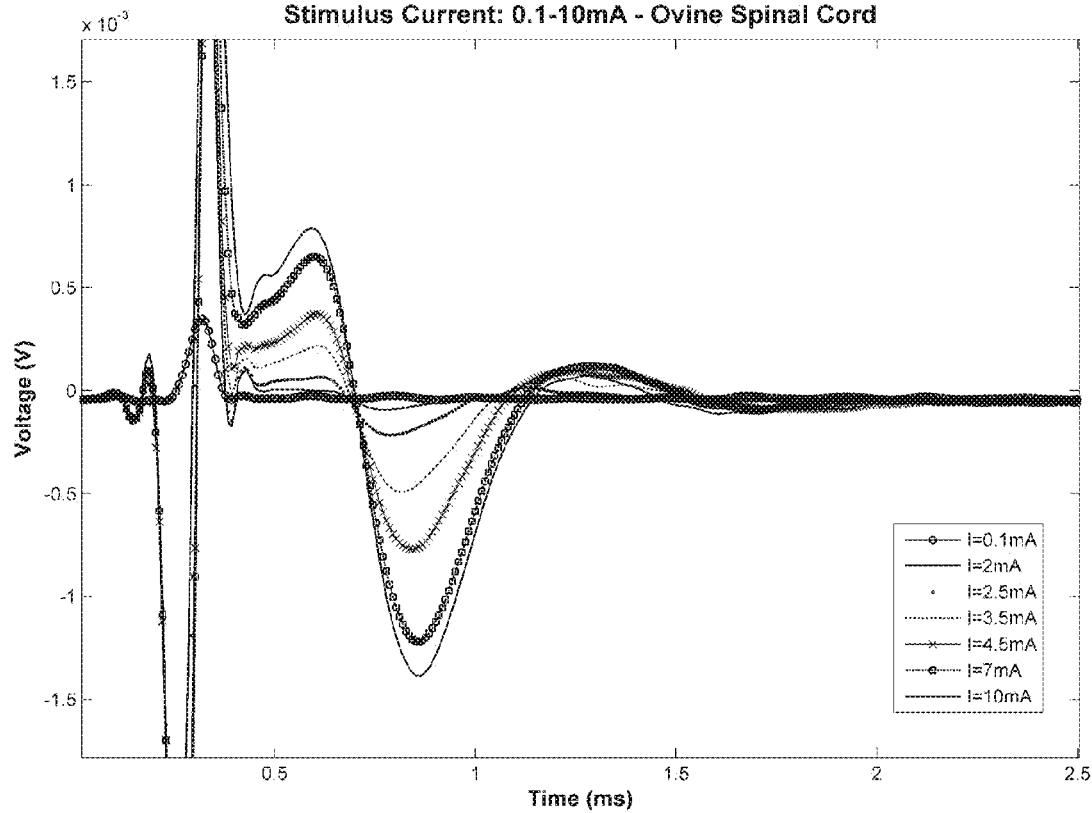
FIG. 5 illustrates ovine compound action potentials resulting from successively applied stimuli of varying amplitudes, in order to ascertain suitable threshold and comfort levels.

The present invention may further provide for partly or completely automated device fitting. The amplitude of the evoked response provides a measure of the recruitment of the fibres being stimulated. The greater the stimulus, the more recruitment and the larger the evoked response. A plot of the compound action potentials measured in a sheep spine for a number of stimulus amplitudes is shown in FIG. 5. The peak height varies with the amplitude of the applied stimulus in a consistent (i.e. monotonically increasing) way.

Figure 6:
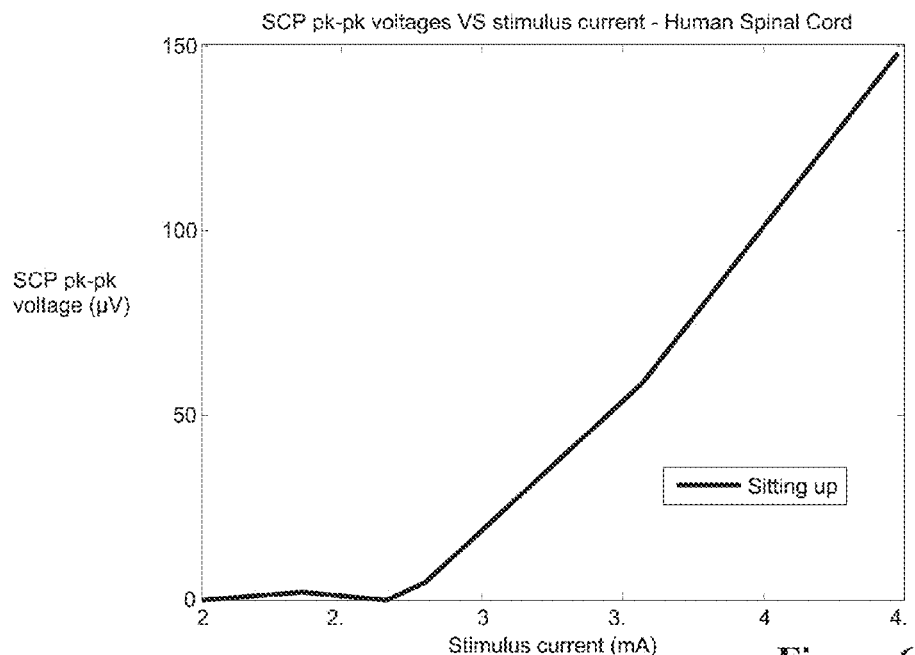
FIG. 6 plots measured spinal cord potential (SCP) amplitude arising from biphasic stimuli of width 120 µs, each stimulus having a current level in the range 0-4.5 mA, as measured in a human subject in a sitting posture.

FIG. 6 plots measured spinal cord potential (SCP) amplitude arising from biphasic stimuli of width 120 µs, each stimulus having a current level in the range 0-4.5 mA, as measured in a human subject in a sitting posture. At some amplitude the patient experiences a sensation derived from the stimulus (at a current of 2.75 mA in FIG. 6). The perception threshold corresponds to the appearance of an evoked response. There are a number of factors which can influence the amplitude of the response generated by a fixed set of stimulation parameters, as discussed further elsewhere herein.

The evoked response for the Aβ fibres can be used in a number of ways during the implantation and subsequent programming of the device. These include:

1. Determining the optimal combination of electrodes to generate the desired therapeutic effect;
2. Selection of the stimulus parameters to generate the desired therapeutic effect;

3. Continuous adjustment of the stimulus parameters to remove variations in recruitment induced by movement, or relative movement of the spinal cord with respect to the electrode position; and 4. Minimisation of stimulation side effects Very often during the assessment of patient suitability for spinal cord stimulation, a trial period is undertaken during which an electrode is temporarily implanted in the epidural space above the spinal cord. The CAP measures of the present invention can be recorded during this implantation and may provide sufficient diagnostic indicator of neurophysiological response to warrant the surgeon performing an implant of the full system.

Figure 7:
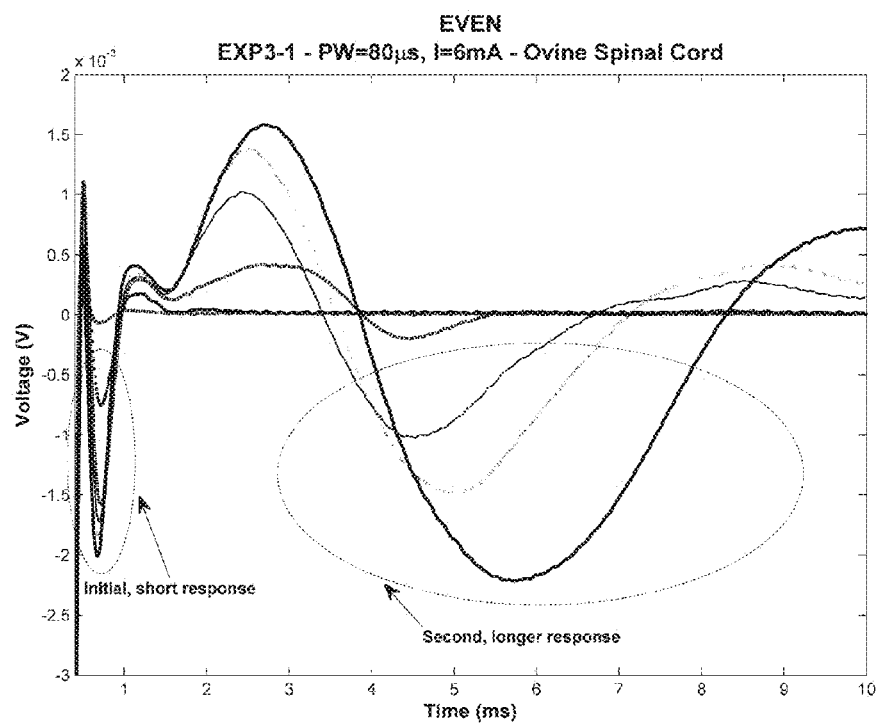
FIG. 7 illustrates the two major response types in an evoked SCP.

The evoked response recorded from the epidural space in the spinal cord varies with the stimulus amplitude and has two components at high amplitudes. It consists of an immediate response (short duration characteristic of the response from fibres with a high conduction velocity), followed by a response with a much longer time scale. The shorter response is characteristic of the recruitment of Aβ fibres in the dorsal column. The response which occurs at longer time scales involves motor system neural responses, EMG, etc. These signal features are shown in FIG. 7.

The normal clinical procedure for adjustment of spinal cord stimulation parameters involves adjustment of pulse width, current and rate to place an induced paraesthesia over the site of pain. There is an upper limit to the intensity of the stimulation, beyond which the patient will not accept further increases, referred to as the dose limit. For some patients this point also corresponds to the point where effective paraesthesia is present and there is good pain relief, however for some, the side effect of the stimulation is intolerable for the patient. Overstimulation of Aβ fibres is also unpleasant for the recipient and unfortunately results in poor efficacy because, although good coverage is obtained, the patient cannot take benefit from the treatment because the side effects are too severe.

The fibre types that are responding at the dose limit have been assessed from patient feedback of the sensations induced. Selected results include:
  56% of patients reported the sensations which are typical of Aβ responses.
  15% reported Aδ typical sensations.
  6% reported C fibre responses.
  21% reported sensations corresponding to motor muscle spinal responses.

The Aβ fibres are large in diameter (13-20 μm) and much larger than Aδ fibres (1-5 μm) and C fibres (0.2-1.5 μm). The C fibres have the slowest conduction velocity 0.5 to 2.0 m·s$^{-1}$ whereas Aδ fibres have conduction velocity of 3-30 m·s$^{-1}$.

Considering the propagation velocity of recruited Aδ fibres ascending the spinal cord is 15 m·s$^{-1}$, and a typical distance of a spinal cord electrode array is 7 cm long, the propagation delay from one end of the electrode array to the other is 4.6 ms.

Figure 8:
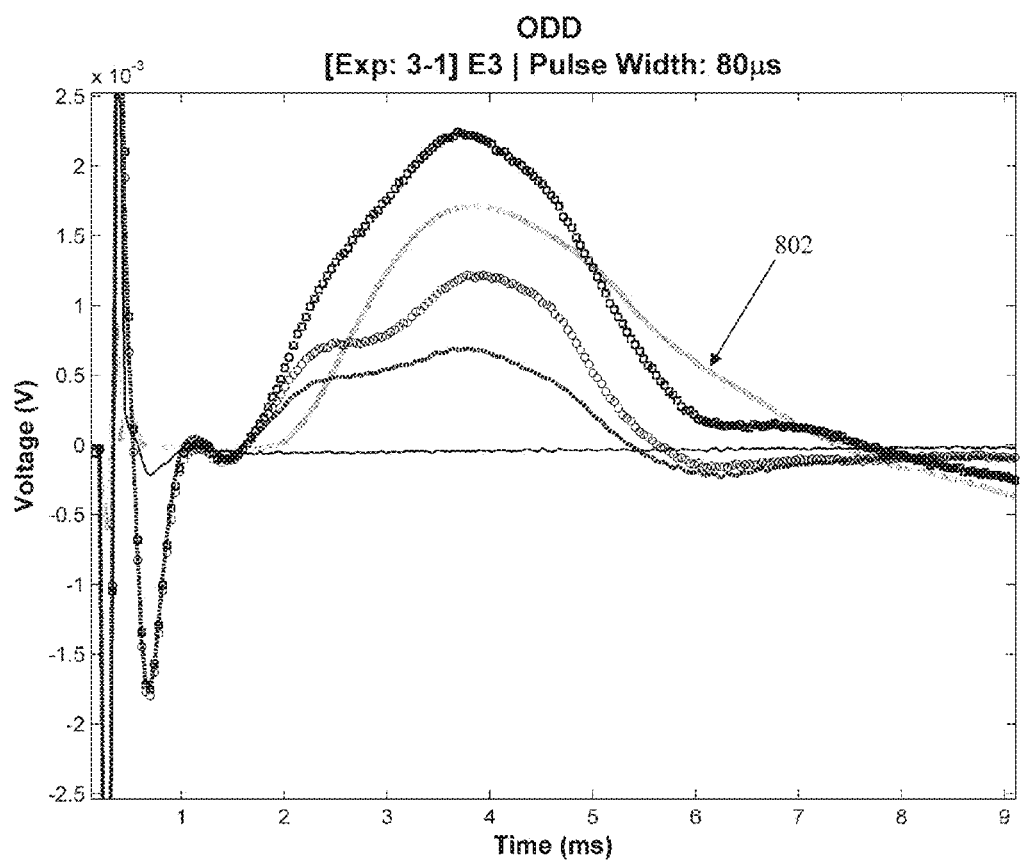
FIG. 8 illustrates measured ovine evoked responses demonstrating fast and slow responses, together with an electromyogram (EMG) trace recorded from an electrode implanted in the corresponding muscle.

FIG. 8 illustrates the evoked response in a sheep spinal cord, demonstrating fast and slow responses. The trace 802 is an electromyogram (EMG) trace recorded from an electrode implanted in the corresponding muscle. The Aβ activity is present in the 0 to 1.5 ms time window. Above a threshold stimulation current level, a slow response is observed 2 ms after stimulation. The slow response is the result of the activation of other neural elements. Activation of the Aδ fibres results in activation of the spinal reflex loop (nociceptive reflex) and can cause muscle contractions. Direct activation of motor neurons also will cause motor responses. Observation of the slow responses in animal experiments was accompanied by the observation of muscle twitching, while observation of the slow response in humans is observed only at uncomfortable stimulation levels. Accordingly, embodiments of the invention may use the existence of a slow response as shown in FIG. 8 as the or a feedback variable, in relation to which the therapy map defines that the control variable should be at a level which does not give rise to any slow response, or any slow response above a threshold, to effect comfortable therapy.

The present embodiment thus recognises that evoked response measurements such as those of FIG. 7 can be used to determine the allowable dynamic range of stimulation which is available to the patient, and further may be used to verify that ongoing stimuli are delivering a desired therapy. In this embodiment, the presence of the slow response is automatically detected by the implanted device, by looking for an evoked response which has a peak from around 3 to 4 ms after the start of stimulation. The slow response is an indicator of the recruitment of fibre classes other than the target Aβ fibres and is accompanied by side effects which are undesirable. The dynamic range available to the patient can thus be determined by using the onset of a slow response as an indication of an upper limit to the stimulation settings. The slow response can be brought on and measured either during normal use of the device or under general anaesthesia, by adjusting the stimulus level until the slow response characteristic emerges in the measured neural response, indicating that the comfort threshold has been reached. This procedure can be conducted on each electrode of the array, various combinations of electrodes, and in a number of different postures of the patient. A maximum safe stimulation level may then be set in the patient's controller for each electrode.

In providing an automated method for controlling the stimuli applied over time, the present embodiment recognizes that the ideal control variable is the number of fibres recruited ($R_N$). At a constant electrode array to cord distance d the measured Aβ amplitude is proportional to recruitment. However as the sense electrode to spinal cord distance d changes, for a constant $R_N$ the measured Aβ amplitude varies and is inversely proportional to the square of the distance. Further, as the distance from the stimulus electrode to the spinal cord changes, the stimulation current required to activate a given $R_N$ is proportional to the square of distance. Thus the present embodiment recognizes that, unless patient sensitivity is small, it is unlikely that controlling the measured Aβ amplitude to be constant will maintain constant recruitment $R_N$. Instead, when the electrode array is closer to the cord it is typical that the measured Aβ amplitude should be controlled to be higher in order to effect constant recruitment $R_N$, and when the electrode array is more distal from the cord it is typical that Aβ amplitude should be lower to continue to effect constant recruitment $R_N$.

Figure 19:
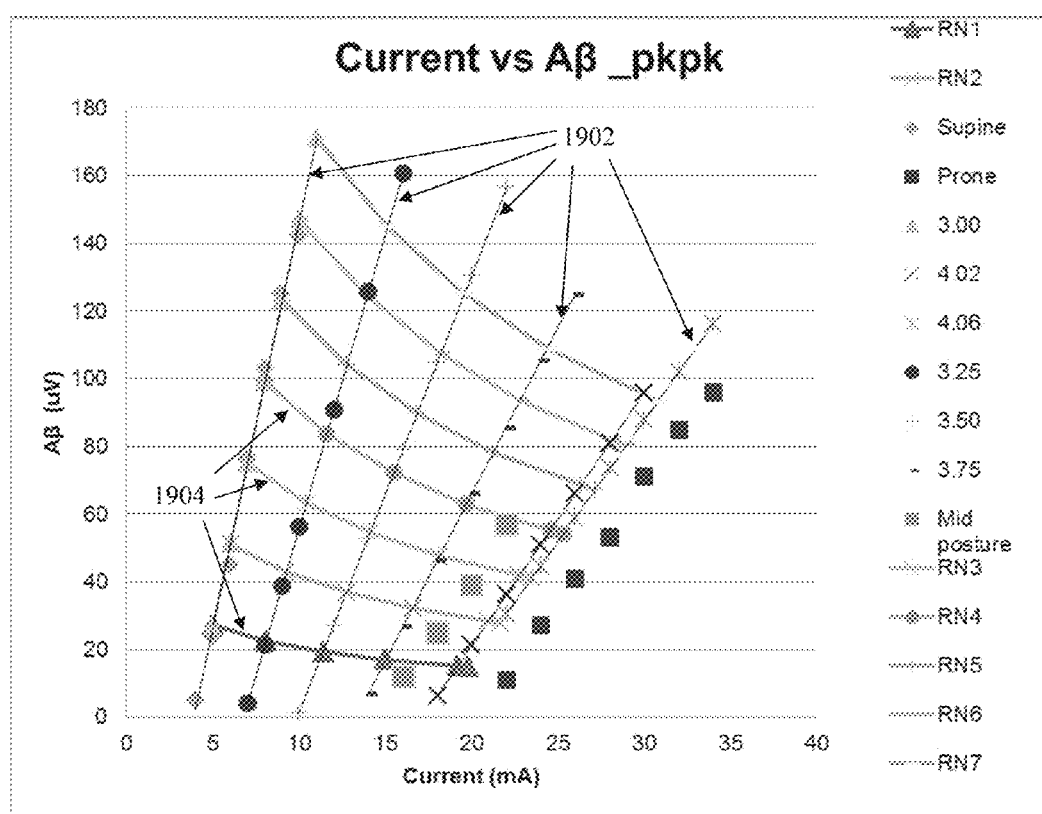
FIG. 19 is a plot of multiple curves, each curve reflecting the measured Aβ amplitude for a stimulus amplitude sweep, while a user is in a single posture, with each curve reflecting a different user posture.

FIG. 19 is a plot of multiple curves 1902, each curve reflecting a set of Aβ amplitude measurements for a stimulus amplitude sweep, while a user is in a single posture, with each curve reflecting a different user posture. A second set of curves 1904 give an example of the curves of constant therapeutic benefit for one sample user, one of which is the preferred curve of therapeutic benefit which it is desired to approximate by a suitable therapy map. While the curves of constant therapeutic benefit 1904 in FIG. 19 are monotonic decreasing it is noted that the profile of such curves can vary considerably between users, and for example may have positive slope and/or may not be monotonic. The therapy map is defined in a manner which reflects these curves for the individual implant recipient, and so device fitting includes a determination of the desired curve of therapeutic benefit for the user concerned. It is noted that in FIG. 19 the Aβ amplitude response curves 1902 for the prone, mid-posture and supine postures is actual Aβ amplitude response data obtained from a human subject, while the other curves 1902 are synthesized data.

Figure 20:
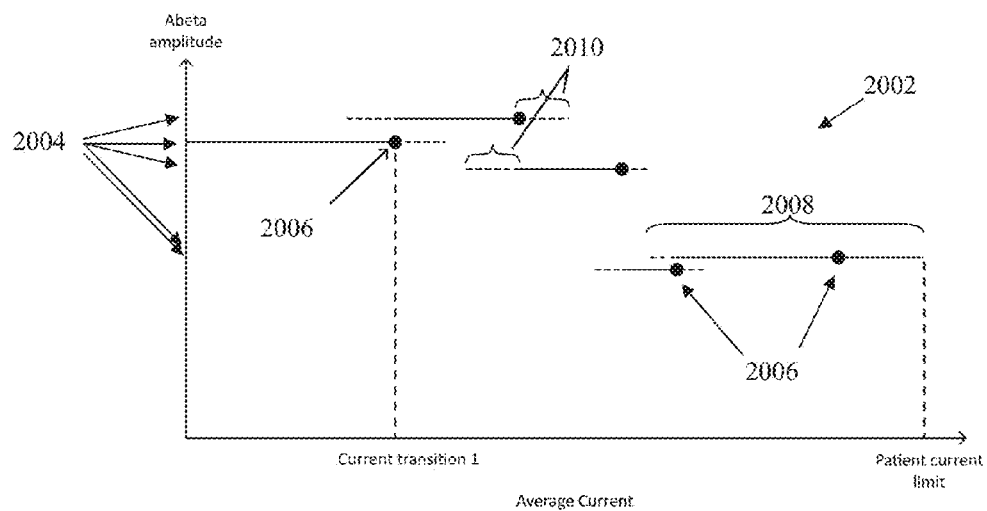
FIG. 20 is a plot of the therapy map of a preferred embodiment, the therapy map defining a stepped relationship of desired output measured response to input stimulus intensity, with hysteresis.

To provide a therapy map which best approximates the desire curve of therapeutic benefit, the embodiment of FIG. 20 provides a therapy map 2002 which has a number of different target feedback variable values 2004, one of which is chosen at any given time based on the average control variable value. Parameters requiring selection are feedback target values, with a control variable value transition point, and a hysteresis band; and a period of averaging of the control variable to determine the feedback target selection. In FIG. 20 the feedback variable is Aβ amplitude, and the control variable is the average input stimulus current.

The therapy map 2002 is derived by first obtaining "comfort points" 2006, by adjusting the current to the patient's comfort level, for several different postures. The Aβ amplitude arising from that comfort point is then measured, and defined in the therapy map as a suitable target Aβ amplitude 2004. A stimulus intensity band 2008 associated with each comfort point 2006 is defined either side of the comfort point and each band 2008 is of a width which encompasses some or all of the distance to the next comfort point. A hysteresis band 2010 is effected by overlapping the bands 2008, so that the feedback target 2004 does not oscillate quickly between two values at times when the stimulus intensity is near the edge of two bands 2008.

Figure 12:
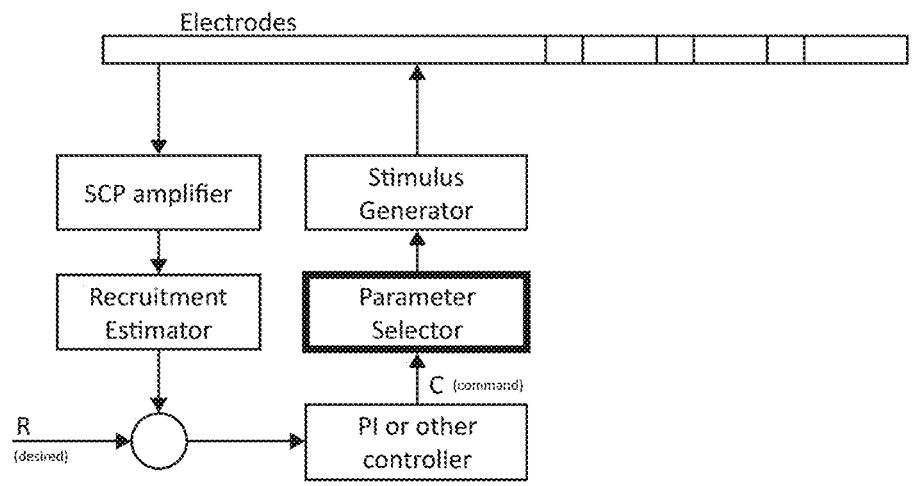
FIG. 12 is a schematic of a feedback controller to effect stimulus control in response to recruitment of neurons.

The method for controlling the stimuli, for example implemented using the device of FIG. 12, continually looks for error between the actual measured Aβ and the current target level 2004 as defined by the therapy map. The instantaneous stimulus current (ie the stimulus current of the very next stimulus pulse) is adjusted accordingly, perhaps in a moderated fashion to effect a desired stimulus slew rate as discussed further in the following. At times when the averaged past stimulus current of the last 100 stimulus cycles strays outside the current hysteresis margins of band 2008, the target 2004 is changed to the level corresponding to the adjacent stimulus intensity band 2008. Thus, when the patient moves, the average stimulus current value provides an indication of their activity/posture, and this in turn changes the target feedback value 2004 to the point where the patient experiences maximum comfort for that given activity/posture.

Figure 21A:
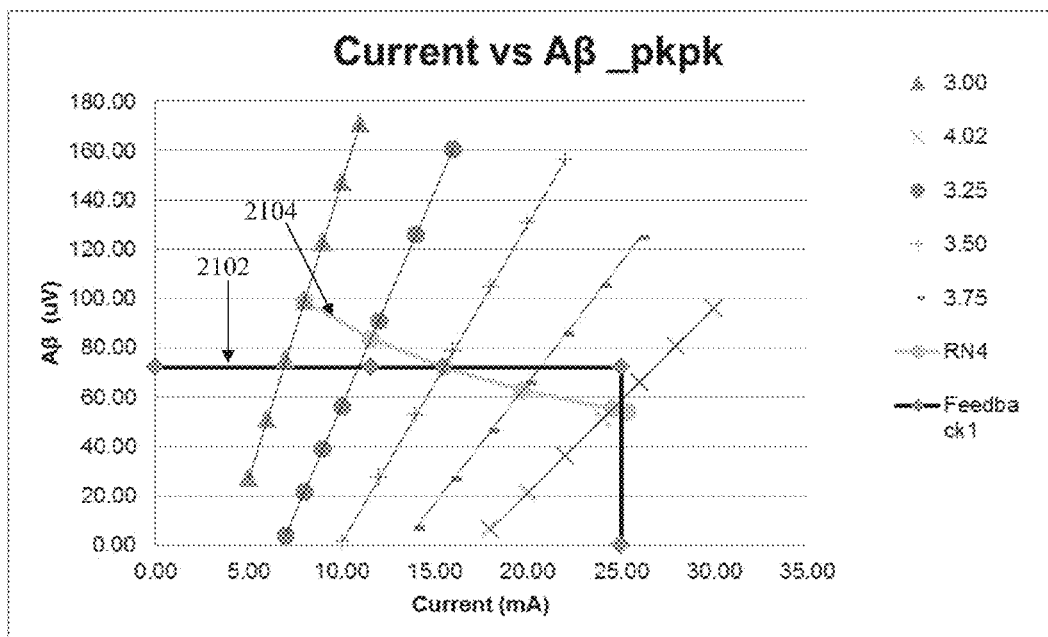
FIG. 21a illustrates a therapy map of an alternative embodiment, in which constant recruitment $R_N$ is approximated by constant measured response amplitude.

While FIG. 20 shows a preferred solution, other methods of control may be provided in other embodiments of the invention. For users with wide tolerance, a flat therapy map may provide a sufficiently accurate approximation of the desired curve of therapeutic benefit. This map is effected by a fixed Aβ amplitude target for all stimulus levels up to a maximum allowable stimulus level. This approach is shown in FIG. 21a & b with locus 2102 being the therapy map. Relative to the optimal curve 2104 the flat therapy map 2102 will under stimulate at small distances to cord and over stimulate at large array-to-nerve distances.

Figure 21B:
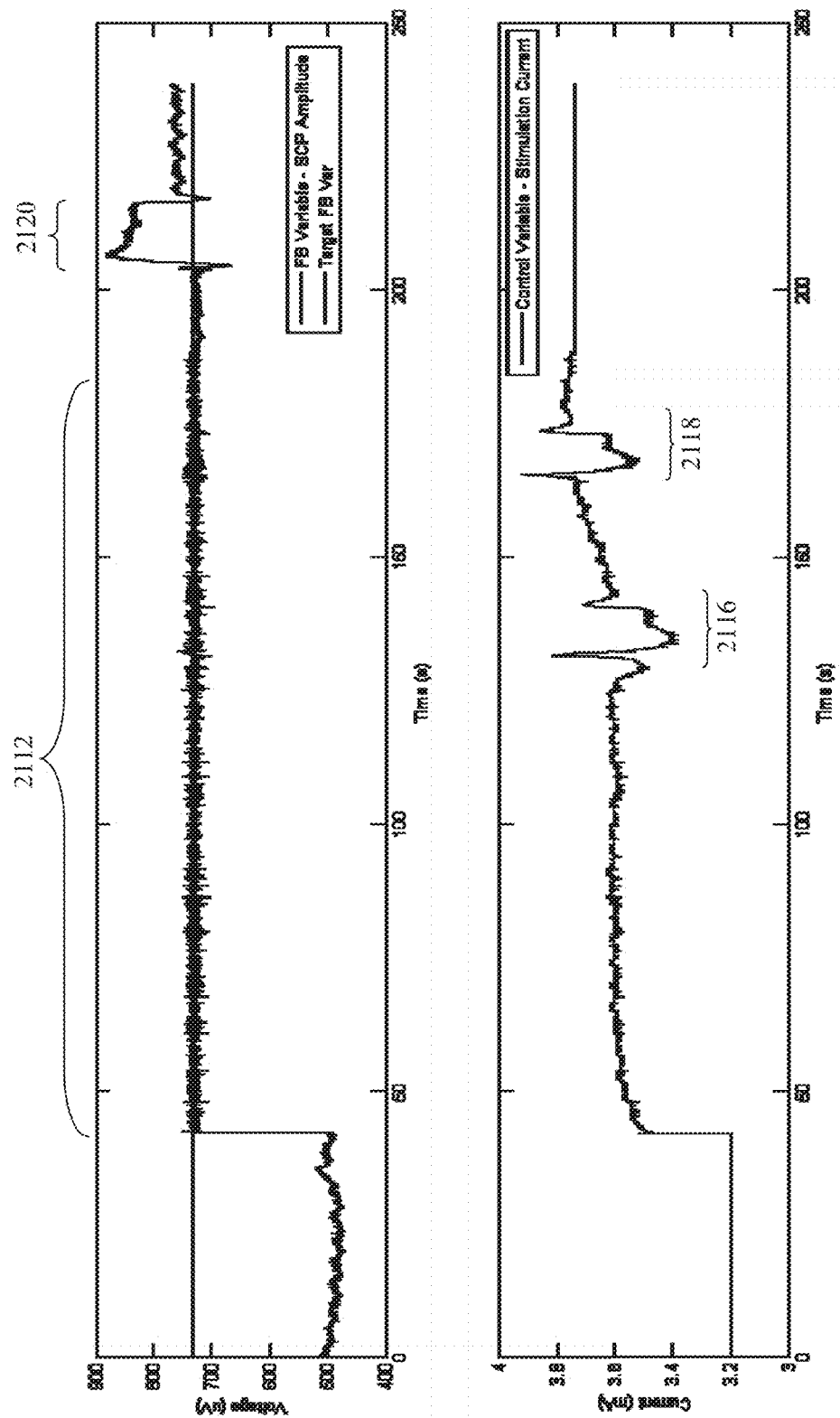

FIG. 21b illustrates results obtained when the therapy map of FIG. 21a was implemented in an ovine subject. The upper plot in FIG. 21b is the Aβ amplitude which, during the operational feedback period 2112, was used as the feedback variable. The lower plot shows the stimulation current which resulted during a feedback period 2112 and then during a non-feedback period 2114. Notably, at moments 2116 and 2118 the sheep's head moved, causing the feedback loop to make substantial variations in the stimulus current applied, in order to maintain the target Aβ amplitude. During these periods no significant deviation of the Aβ amplitude away from the target value occurred, revealing the efficacy of the method of the present embodiment at maintaining constant evoked response amplitude even during postural changes. After period 2112 feedback control was disabled and a constant stimulus was then applied. As can be seen, in the post-feedback period the constant stimulus evokes an Aβ amplitude which varies significantly with movement at 2120.

Figure 22:
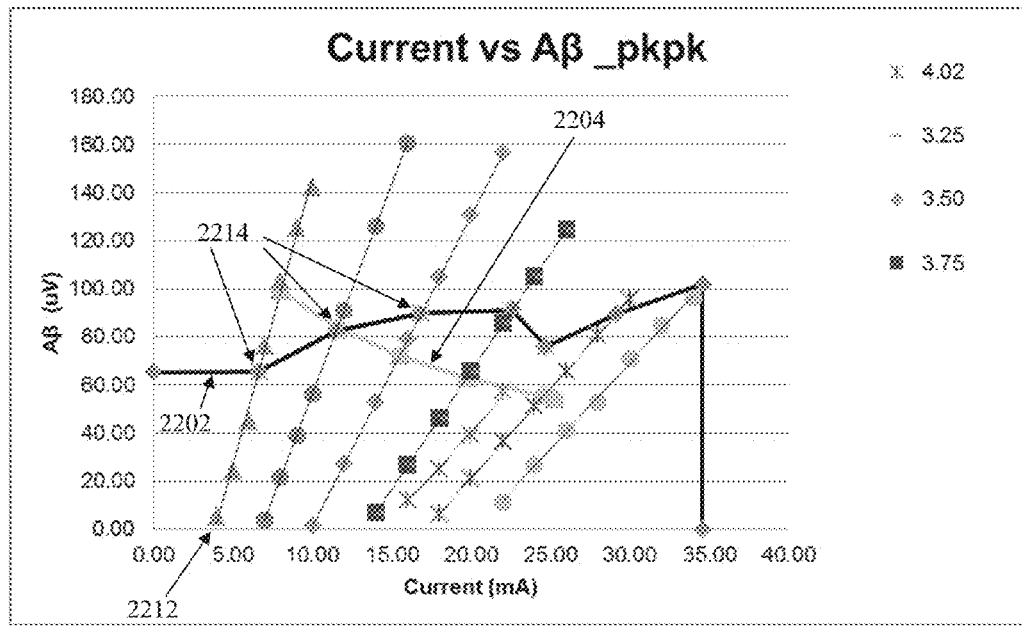
FIG. 22 illustrates a therapy map generated in an automated manner by linear interpolation between set points, each set point being a multiple of a threshold stimulus.

In yet another embodiment, the therapy map is derived from the threshold current value at each posture, as shown in FIG. 22. Under this approach, for a given posture the Aβ amplitude is measured in response to 2 stimuli of different intensity which are in the linear range of the Aβ amplitude response curve, as discussed elsewhere herein with reference to FIGS. 13, 15, 16, 17 and 18. The threshold current $I_T$ (shown at 2212 in FIG. 22) for this posture is multiplied by a predetermined constant K to derive a point 2214 on that particular Aβ amplitude response curve which is entered into the therapy map 2202. As the user changes posture, either when asked by a clinician or by fitting software, or simply of their own volition at later times, further points on the therapy map 2202 are determined in like manner by reference to the respective threshold current. In this embodiment the therapy map is completed by a piecewise linear interpolation between the points 2214, however the therapy map could alternatively be a best fit linear solution or smoothed curve derived from the set points 2214, or a stepped response with hysteresis of the type shown in FIG. 20.

Figure 13:
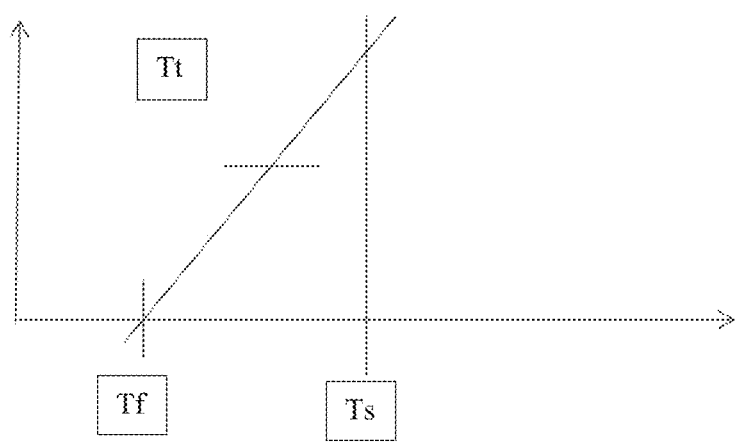
FIG. 13 is a plot of a linear approximation of the SCP growth curve (evoked response amplitude vs. stimulus current), indicating the relationship between various threshold levels.

To further describe the generation of each point in FIG. 22, we refer to FIG. 13 which is a plot of the SCP growth curve (Aβ amplitude vs. stimulus current), indicating the relationship between various threshold levels: Tf, the threshold for fast response; Ts, the threshold for slow response; and Tt, the threshold for therapeutic response. For automated feedback control, the therapeutic stimulus level is initially set at some point between Tf and Ts. For the initial setting an initial ratio Ri is determined which places Tt between Tf and Ts.

$$\frac{Tt - Tf}{Tf - Ts} = Ri$$

Then for any subsequent stimuli $$Tt = Ri*(Ts-Tf)+Tf$$

The stimulus which is used to probe the slow response presence or absence is output at frequency which is not annoying to the recipient. The fast (<2 ms) response recorded is due to activation of Aβ fibres in the spinal cord, and the slow response observed accompanies unwanted, uncomfortable or undesirable stimulation (e.g. muscle fibre activation). Thus, the stimulus level should ideally be set between the fast response threshold value (Tf in FIG. 13) and the value at which an unwanted response is evoked.

Figure 23:
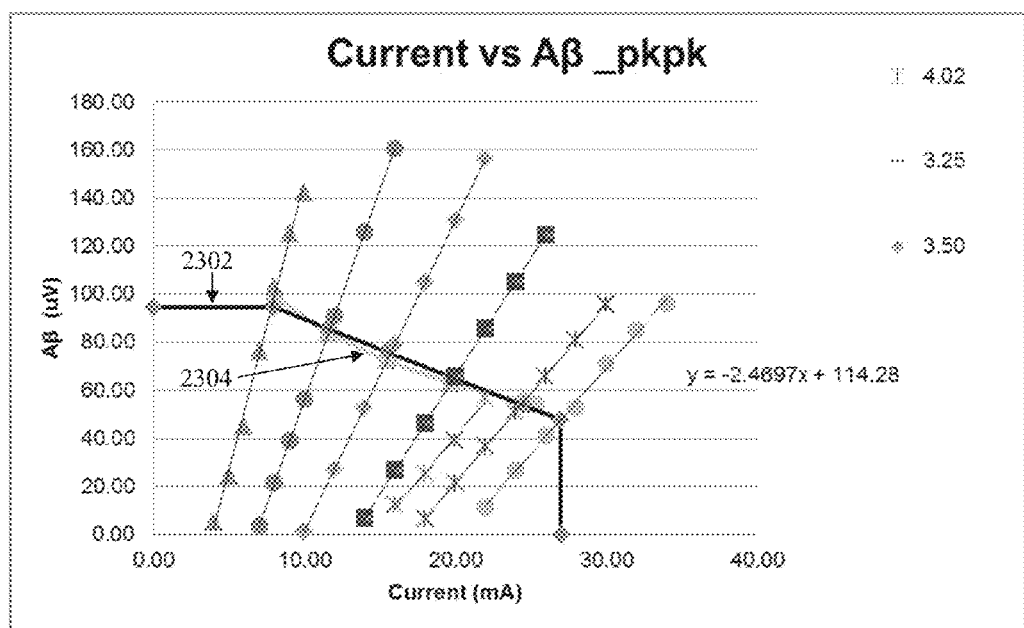
FIG. 23 illustrates a therapy map generated by a linear approximation of an optimal therapy and limited at low stimulus values by the maximum allowable measured evoked response strength and limited at high stimulus values by a maximum allowable stimulus intensity.

FIG. 23 illustrates a further embodiment in which the therapy map 2302 is configured to approximate the desired curve 2304 by use of a linear relationship: Aβ=m*I+b, constrained by a maximal Aβ level for small currents and also constrained by a maximal stimulus current. The coefficient m is negative in this embodiment. In this embodiment the user is given ongoing control over stimulus strength (b) and posture sensitivity (m).

Once again, while the map 2302 is only an estimate of the actual desired relationship 2304, the error may be within patient perception limits and also within the limits of measuring Aβ reliably.

Figure 24A:
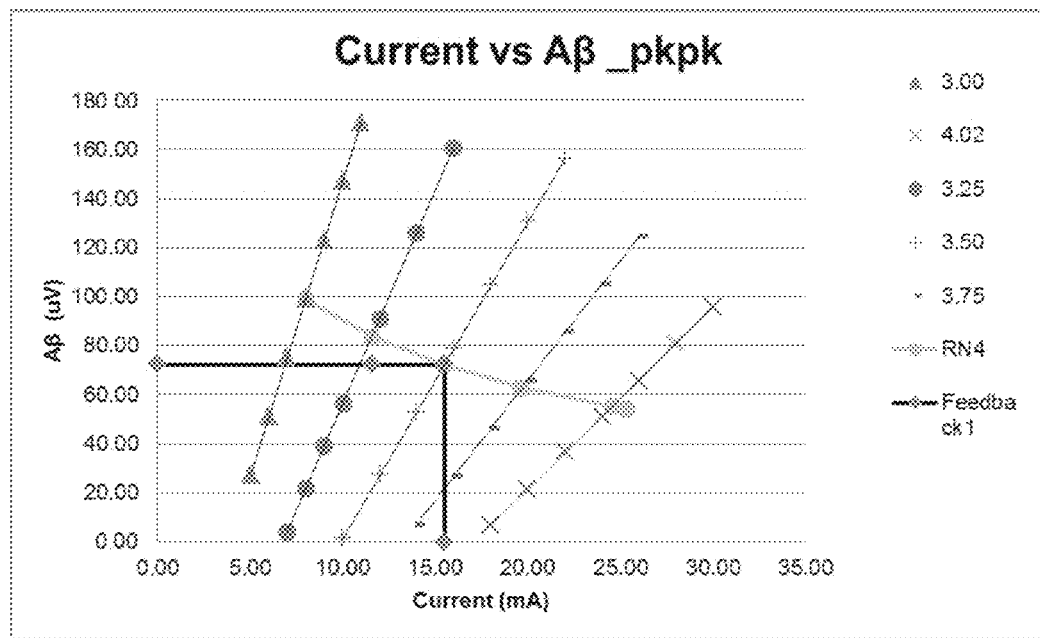
FIGS. 24a to 24d illustrate automated derivation of a therapy map in response to user input of preferred stimulus intensity at different times.
Figure 24B:
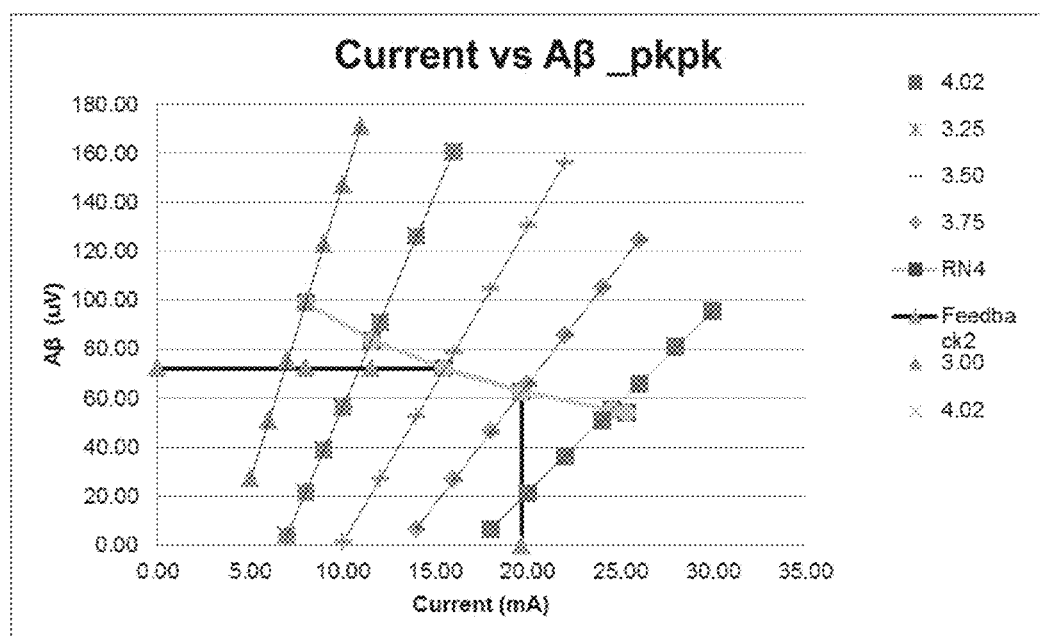
Figure 24C:
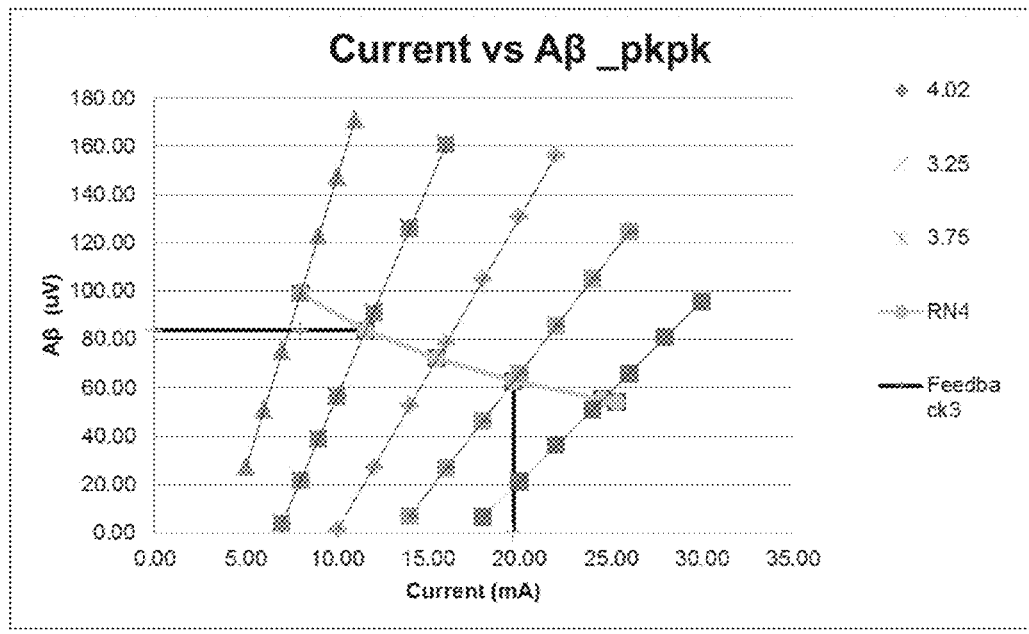
Figure 24D:
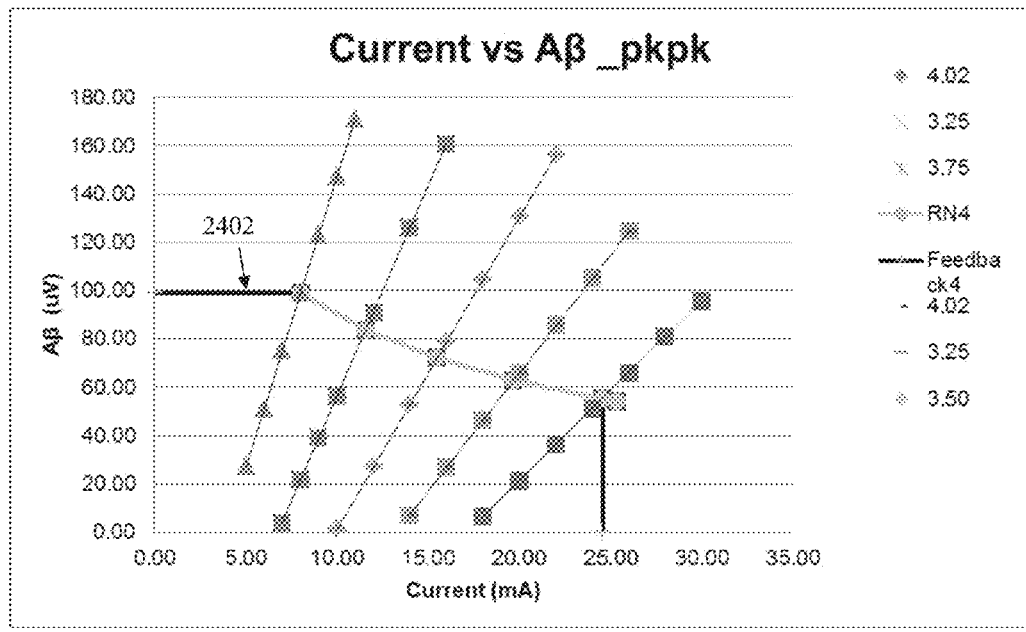

FIGS. 24a to 24d illustrate another embodiment, in which a therapy map is developed in response to user input. The device is initially configured with a flat therapy map of the type shown in FIG. 21a. However, as the user begins to use the device, the user's preferred settings for each posture are monitored by the device in an automated manner. The therapy map derivation needs no knowledge of what is the user's actual posture. Rather, whenever the user elects to input a change in stimulus amplitude (usually, in response to a change in posture), the controller derives a further point on the therapy map from that user input. The controller observes the preferred stimulus current as set by the user, and observes the measured evoked Aβ amplitude resulting therefrom, as shown in FIG. 24a. To ensure that the user input is reliable, the system allows time for the Aβ response to settle after the patient adjusts current to ensure that the patient is satisfied with the new setting. If the user quickly changes the setting it is deemed non-preferred and discarded; if not, the new set point is deemed to be desirable and is built into the therapy map. The next time the user changes posture and inputs a new preferred setting, the therapy map can be updated with a new set point by observing the new preferred stimulus current as set by the user, and by observing the measured evoked Aβ amplitude resulting therefrom, as shown in FIG. 24b. This process continues as shown in FIGS. 24c and 24d, so that the therapy map is progressively defined simply by the system watching what settings the user imposes at different times, as shown in FIGS. 24a-d. Once the set points from patient input are defined the therapy map is completed by linear interpolation between these points, and by applying a maximum Aβ amplitude at low stimulus currents, and by imposing a maximum stimulus current value. The patient-defined points in therapy map 2402 can be defined in the clinic, manually by the user following a fitting programming sequence at home, or even automatically without the user needing to do anything other than adjust the stimulus intensity whenever they feel the need to do so. The need for the user to manually adjust the stimulus intensity should then reduce significantly once the therapy map is appropriately defined from initial patient inputs.

Recipients of spinal cord stimulators often report movement-related side-effects of using their systems. If they move in such a way that their implanted electrode moves closer to their spinal cord, they will experience an increase in intensity of the stimulus. Similarly if the electrode moves further from their spinal cord, they will experience a decrease in stimulus intensity. The over-stimulations can be extremely uncomfortable and potentially dangerous for the user. Understimulation for a prolonged period may result in the re-emergence of the user's underlying chronic pain, but is generally less severe than overstimulation. As such there is a difference in the severity and time-frame of side-effects depending on whether the system is under- or over-stimulating. Thus, in preferred embodiments the control loop is used so that the stimulus is constantly adjusted to cater for such side-effects, but in a different manner depending on whether the feedback is acting to increase or decrease stimulus intensity.

In this embodiment this is effected using differential gains and slew rates. For differential gain the feedback gain, being the relationship between the feedback variable error from its target value (FBVE) and the resulting control variable change, is set to a different value for positive or negative FBVEs. For differential slew rate limits the maximum change in control variable allowable is also set to two different values, depending on whether the FBVE is positive or negative.

Figure 25A:
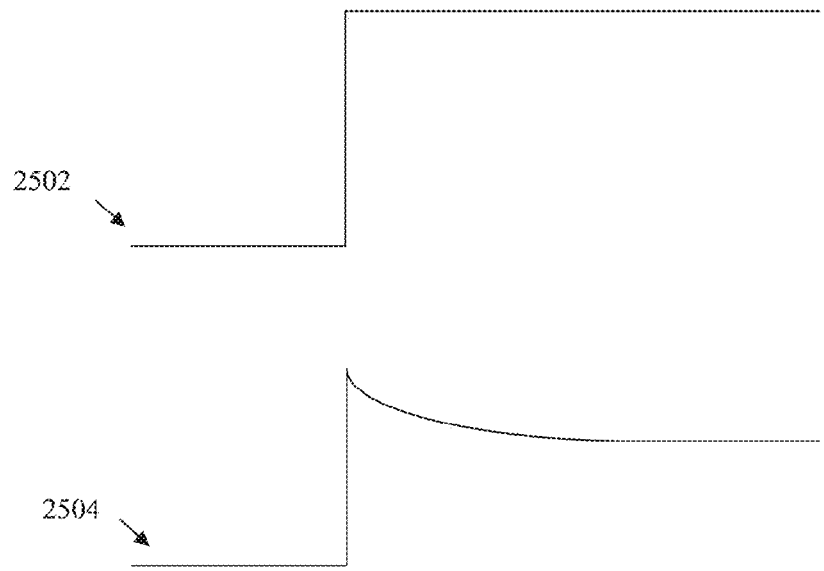
FIGS. 25a and 25b illustrate a preferred manner of applying changes in stimulus intensity, in order to allow for neural adaptation.
Figure 25B:
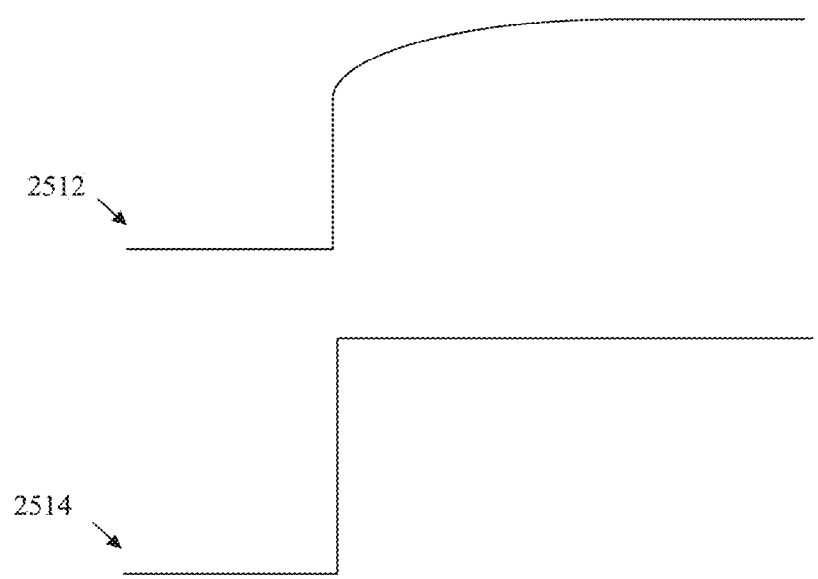

It is noted that the effect of neural "adaptation" in response to a given stimulus can cause an initial recruitment level 2504 to wane in the seconds and even minutes after first applying the change in stimulus 2502, as shown in FIG. 25a. Accordingly, in preferred embodiments when the feedback loop indicates a required change in the recruitment level, a change in stimulus parameters is preferably adapted as shown at 2512 in FIG. 25b over the second and minutes after the change is implemented in a manner which compensates for adaptation, to produce a more step-like change in Aβ amplitude 2514. Indeed, such a stimulus profile can be seen in the region of 40-60 seconds in the lower plot of FIG. 21b.

Embodiments of the present invention may further give an estimation of constant neural recruitment. The electrically evoked compound action potential is a measure of the level of excitation of nerve tissue being excited. The ECAP is the result of the summation of single fibre action potentials from a large number of fibres. The ECAP magnitude depends on the number of fibres and their distance from the sensing electrode. Fibres which are far away from the sense electrode will contribute less to the ECAP due to the strength of the coupling between the sense electrode and the fibre.

Neuromodulation is used to describe the electrical stimulation of tissue in order to produce a therapeutic effect. Passing a current through the tissue and generating action potentials to produce the therapeutic outcome. The number and strength of action potentials in response to the current is not always proportional to current and depends on a number of factors:

The refractory period of the neurons in the nerve
The temperature
The distance from the electrode to the nerve There can be large shifts in the level of recruitment with changes in separation between electrode and tissue, indeed such shifts can take stimulation parameters from sub threshold to above the therapeutic benefit range. This occurs frequently with spinal cord stimulators where an electrode is implanted in the epidural space and the stimulation target is near the dorsal horn of the spinal cord. The separation between the electrode and the target tissue varies with changes in posture. To address this, embodiments of the present invention may measure the strength of the evoked response and use this as the feedback point for control of the stimulus levels. The measured ECAP potential is proportional to the level of neural recruitment and a scaling factor which relates to the separation (and intervening tissue properties) of the sense electrode from the neural elements. In order to generate a target value in order to perform the feedback control, the variation of the signal due to the separation from the electrode must be removed.

The present invention presents a number of methods by which to extract the level of recruitment of the underlying tissue, independent of the separation of the sense electrode. The evoked response recorded for the Aβ fibres from the spinal cord is illustrated in FIG. 6. The amplitude of the response can be characterized by the P2–N1 peak, the N1 peak alone or by the P2 peak alone.

Figure 14A:
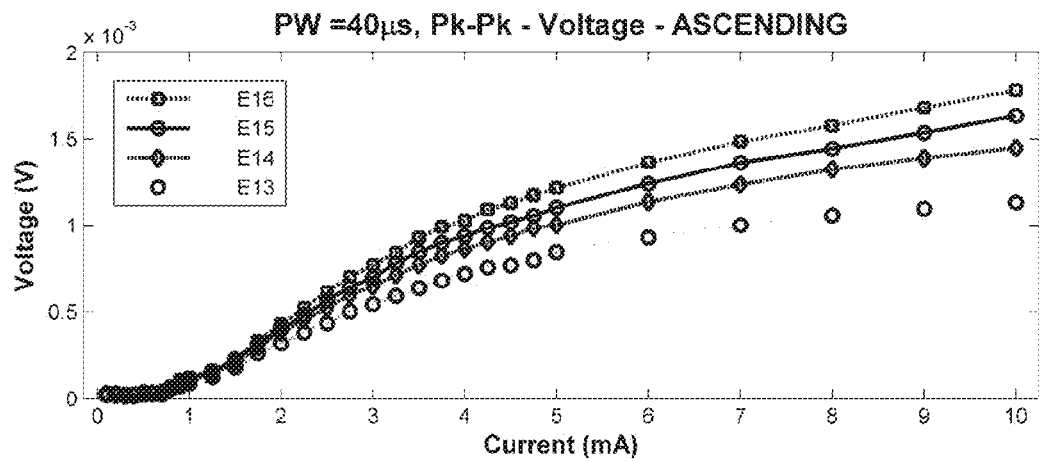
FIGS. 14a and 14b respectively plot the ascending and descending evoked CAP N1-P2 amplitudes each measured on four sense electrodes, recorded in sheep with biphasic 40 µs pulse widths
Figure 14B:
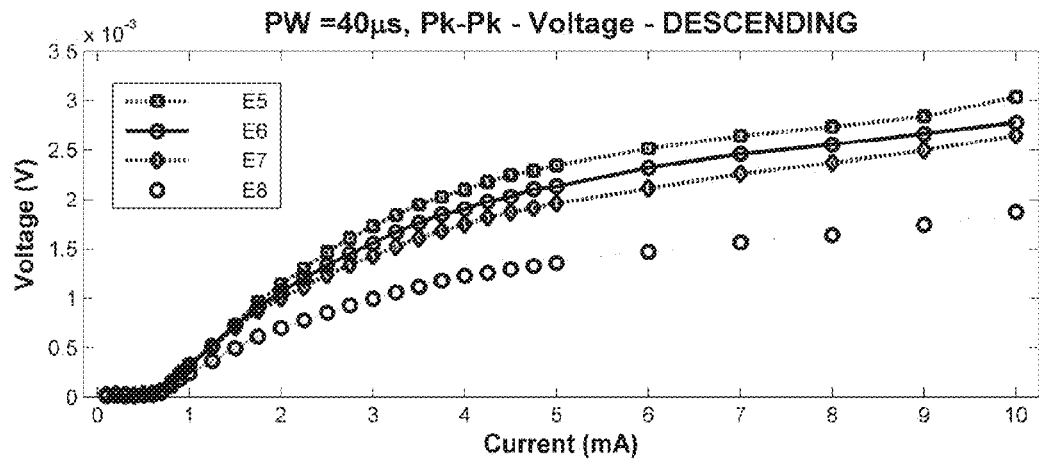
Figure 15:
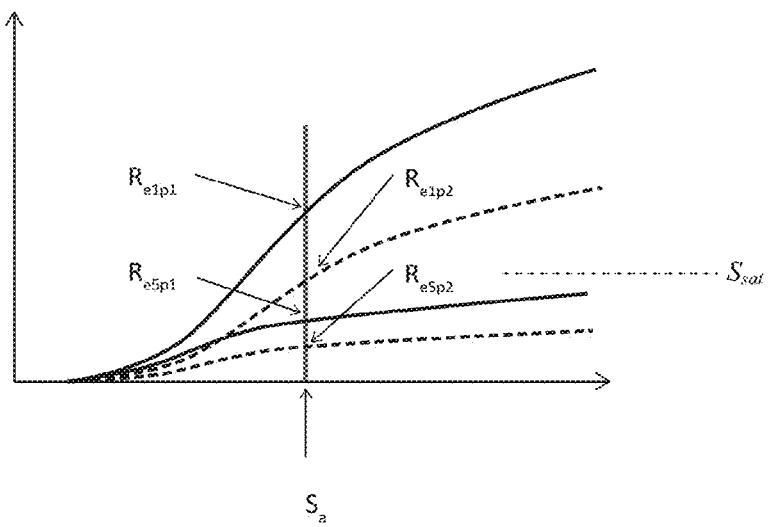
FIG. 15 illustrates respective SCP amplitude response curves, for two sense electrodes which are spaced apart along the spinal cord, and which are at different distances away from the spinal cord.

A first embodiment for estimating recruitment in the presence of varying electrode-to-fibre distance d, is based on relative amplitudes found in measurements at two electrodes. The amplitude of the evoked response varies with the applied charge and the response can be measured on a number of different electrodes distant from the electrode where the stimulus is applied. The responses measured in the sheep spinal cord are shown in FIG. 8, for responses in the ascending direction (i.e. for electrodes positioned away from the stimulating electrode along the midline of the spinal cord). FIG. 14a displays the variation in evoked SCP amplitude with Varying stimulus current, on four separate electrodes in the ascending direction, while FIG. 14*b* showing the equivalent in the descending direction. In particular, FIG. 14 shows ascending and descending evoked CAP N1-P2 amplitudes, recorded in sheep in response to biphasic 40 μs stimulus pulse widths.

The amplitude of the responses for electrodes which are more distant from the stimulus site do not increase as markedly with the stimulus current as the electrodes closer to the stimulus site. The distant electrodes are measuring the propagation of the action potential ascending (or descending the spinal cord) and aren't subject to any localized recruitment phenomena. At a given stimulus level above a critical value $A_{sat}$ the number of fibres close to the sense electrode which can be recorded are all recruited and increasing stimulation no longer causes an increase in the amplitude of the response.

The different sensitivities of the different regions of measurement can be used to estimate the target value for feedback loop control. Consider the responses at two different positions of the electrode relative to the stimulated tissue, in this case the spinal cord. The amplitude response curve in position 1 labelled pl in FIG. 15 for electrode 1 and electrode 5 (sub e1 and e5) are illustrated. For an alternative position p2 the responses are scaled by the effect of the change in distance from the electrode. Less tissue is recruited and less evoked response is measured. The amplitude response of the distant electrodes is only weakly dependent above a saturation level $S_{sat}$ of stimulation on changes to the stimulus amplitude. That is, $S_{sat}$ is an amplitude which is asymptotically approached by the response as seen by electrodes distant from the stimulus.

If a completely flat response above $S_{sat}$ is assumed, then the scaling factor due to the shift in distance for this electrode is simply the ratios of the responses at the large electrode separations (Equation 1).

$$R_{e1p2} = (S_s + A_s) R_{e1p1} \qquad \text{Equation 1}$$

The response measured is scaled by a factor $S_s$ which relates to the changed measurement sensitivity, and by a factor $A_s$ which relates to the change in the amplitude due to the change in the recruitment level. For the case when the amplitude at a distant electrode is weakly dependent on the stimulation current, then:

$$R_{e5p2} = (S_s + A_s) R_{e5p1} \qquad \text{Equation 2}$$

and so $$(R_{e1p2}/R_{e1p1}) - (R_{e5p2}/R_{e5p1}) = A_s \qquad \text{Equation 3}$$

Knowing $A_s$ thus permits estimation of actual neural recruitment from the measured response, even in the presence of varying electrode-to-fibre distance d.

A second embodiment for estimating neural recruitment in the presence of varying electrode-to-fibre distance d, is based on a two point method. The evoked response measured on one electrode has an almost linear dependence on the applied current, in the operating region between threshold and saturation and for a given stimulation pulse width. The response changes (independent of pulse width) with applied charge. If we consider two response curves at two different postures P1 and P2, then they will have different amplitude and saturation point, which will depend on the separation of the electrode from the tissue in each respective posture.

For a fixed electrical activity in the spinal cord the effect of moving the sense electrode away will be to scale the response curve by the factor which relates to the separation. The electrical activity however changes because in this case the sense electrode and the stimulating electrode are both moving with respect to the spinal cord. Movement of the stimulating electrode away from the spinal cord has the effect of lowering the resultant induced electrical activity in the spinal cord because of a reduction in the field strength and this has the effect of shifting the threshold.

Figure 16:
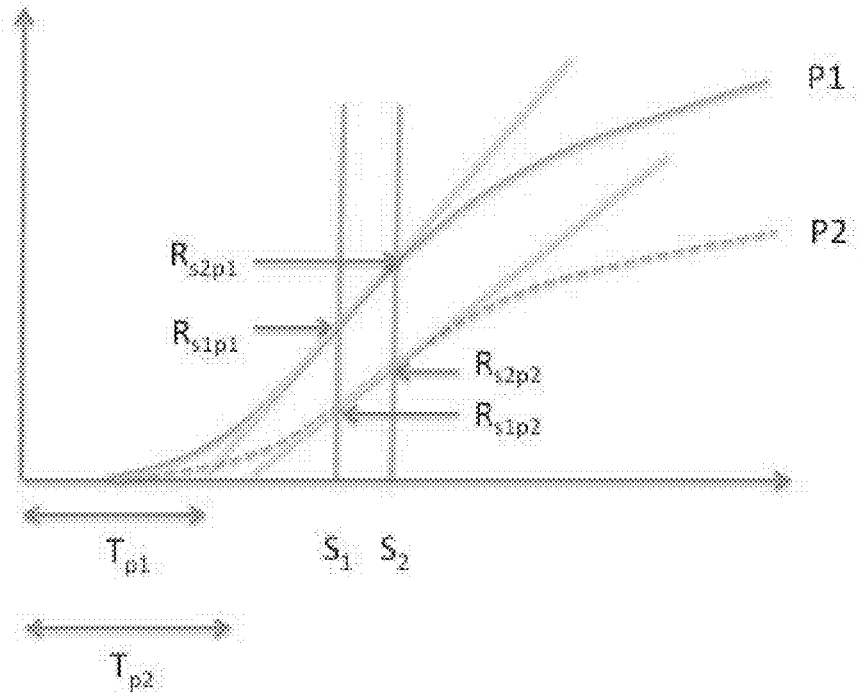
FIG. 16 illustrates theoretical SCP amplitude response curves corresponding to two different postures of the user, in order to illustrate SCP slope determination via a 2-point method.

FIG. 16 shows SCP amplitude response curves for two different postures, indicating slope determination via a 2-point method. The slope and the thresholds of the linear responses can simply be determined from the measurement of the responses at two different current (stimulation) levels in the linear portion of the respective amplitude growth curve. More stimulation levels may be employed to generate more accurate estimates of the slope and the response. For the two different postures P1 and P2 reflected in FIG. 16 the response is measured for two different stimulus intensities S1 and S2, which generate four different responses.

The equation of the respective line is simply:

$$r = R_{s2p1} + ((R_{s1p1} - R_{s2p1})/(S_1 - S_2)) * (s - S_2) \qquad \text{Equation 4}$$

for P1, and $$r = R_{s2p2} + ((R_{s1p2} - R_{s2p2})/(S_1 - S_2)) * (s - S_2) \qquad \text{Equation 5}$$

for P2.

The strength of recruitment is not related directly to the response recorded, due to the influence of the displacement upon the sense electrode. However, the intercept of the line of equation 4 or 5 with the x axis approximates the threshold, i.e. the minimum stimulus at which a neural response arises. The threshold can then be used to establish the stimulus parameter control loop variable to respond to changing d.

$$T_{p1} = R_{s2p1} - ((R_{s1p1} - R_{s2p1})/(S_1 - S_2)) * S_2 \qquad \text{Equation 6}$$

The threshold scales with the influence of the change in electric field as a result of the displacement. In order to achieve a constant level of recruitment the threshold estimate determined in this manner can be used to determine the target response signal for the control loop.

Figure 17:
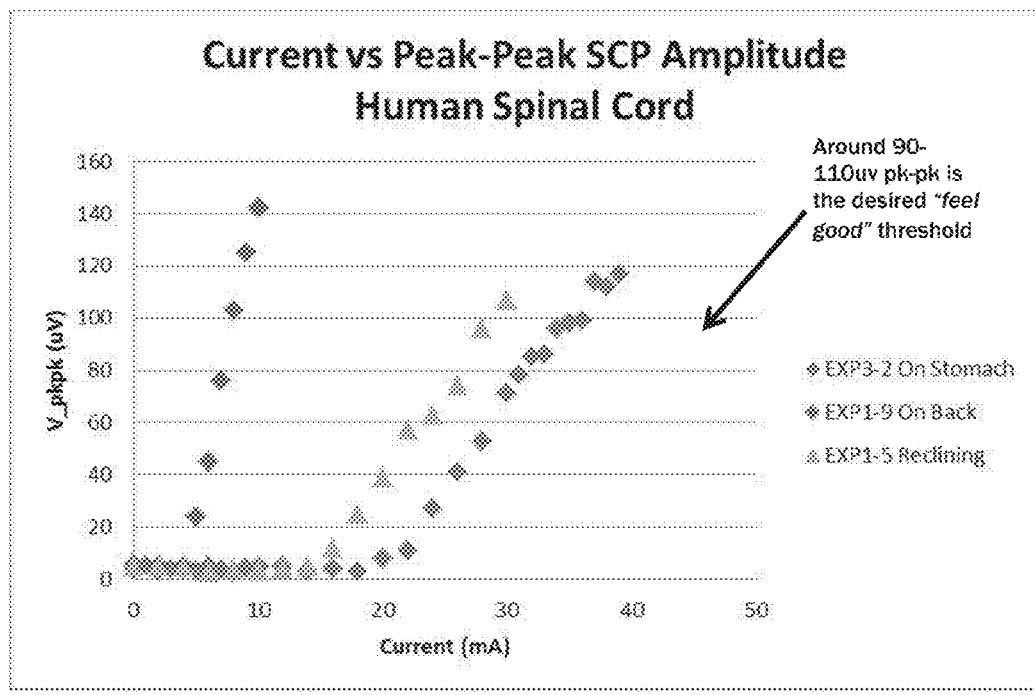
FIG. 17 illustrates three SCP amplitude response curves measured from a human subject in three respective postures.

FIG. 17 shows exemplary data collected from a human subject in three different postures: lying prone, lying supine, and reclining. The peak-to-peak amplitude is plotted against the stimulation current. The threshold values calculated from linear fits to the straight line of the type set out in equations 4 and 5 can be used to estimate the stimulus required to achieve the same level of neural recruitment, independent of the position of the electrode. As can be seen in FIG. 17, the technique of this embodiment of the invention provides strong differentiation between user postures, permitting automated feedback control of changed postures. Moreover, FIG. 17 reveals that if the stimulus was adjusted to give the same amplitude of the measurement of evoked response, the stimulus value would be in error by 20% in the two extremes of the posture.

The stimulus intensity scaled by the threshold value corresponds to a psycho-physical percept of the paraesthesia. For the individual whose data is displayed in FIG. 17, threshold corresponded to sensation on the left leg. The threshold was measured by adjustment of the stimulus intensity and asking the patient to describe the location and strength of the sensation. This task was performed in three different postures, with the patient sitting up, on their back and lying on the stomach, represented in the three rows of Table 1. The first sensation experienced was in the left leg, and the calculated thresholds from linear fits to the lines as per equations 4 and 5 correspond well with the measured thresholds. As the stimulus intensity increased, the range of coverage increased, covering both legs. The stimulus level required to achieve this psycho-physical threshold is different at all the different postures. The stimulation current required to produce an identical psycho-physical response irrespective of the posture can be calculated from the threshold value (for that current posture), multiplied by a scaling factor determined from the measurement at another different posture.

TABLE 1

| Thresholds | Leg | Both Legs mA | Measured | Lower Back | Measured |
|---|---|---|---|---|---|
| 3.9 | 5 | 4.0 | 6 | 6.7 | 10 |
| 14.2 | 12 | 14.8 | 16 | 24.5 | 24 |
| 19.2 | 16 | 20 | | 33 | |

Thus, electrically activated compound action potential can be used to predict the stimulation level required to achieve a constant psychophysical percept.

A further embodiment for estimating neural recruitment even in the presence of varying electrode-to-fibre distance d, is based on peak position within the measured neural response. The recruitment of a nerve fibre in an electric field is a probabilistic event. Increasing the electric field strength increases the probability of firing. The higher the field strength the more likely any one nerve will fire and the firing of those nerves will become more and more synchronised. The result of the synchronisation is a sharpening of the peak and shift of the peak closer toward the stimulus time. The recorded peak will have a shorter interval from the onset of stimulus to peak height for higher stimulation intensities. Peak position thus presents a signal feature which may be analysed to assess actual recruitment.

A further embodiment for estimating neural recruitment even in the presence of varying electrode-to-fibre distance d, is based on spectral characteristics of the measured neural response. As the distance d changes, the fibre-to-electrode transimpedance function shape changes, as can be understood by reference to the cable model of a myelinated axon, for convolutional modelling. A myelinated axon consists of a tube formed of active axonal membrane, sheathed in a layer of insulating myelin. This myelin sheath is interrupted at regular intervals, exposing the membrane to the external medium. These gaps, the nodes of Ranvier, occur at intervals of approximately 100 times the axon diameter, across many types of myelinated nerve. This physical structure permits analysis with a discrete cable model; the inside of the axon is assumed to be a homogeneous conductor, while the membrane ion channel dynamics can be modelled as a nonlinear, time-variant conductance across the membrane at the nodes of Ranvier The change in shape of the fibre-to-electrode transimpedance function in response to a change in d has the effect of smearing the SCP out in time with increased distance, which also reduces its peak-to-peak amplitude. This time-domain change can be measured independently of amplitude, to obtain a direct estimate of distance variation.

The propagating action potential in a single fibre is related to a corresponding action current through the fibre's cell membrane. After the AP is initiated in the fibre, the change in potential at one point in the fibre causes ion channels in the nearby membrane to open and close, permitting the flow of a current which then changes the potential further along. In this way, the action current/potential propagate continuously along unmyelinated fibres (such as C fibres), and jump from node to node along myelinated fibres (such as Aβ and Aδ fibres). Action potentials propagating along many nerves in a bundle give rise to a measurable compound action potential (CAP). This measured potential is the sum of the effects of the individual action currents along each fibre; a strong current into the fibre is seen at the leading edge of the activation, while an out-ward current follows, as the fibre's membrane recovers. This may be modelled, for each point on the fibre, as experiencing a fixed action current waveform, delayed proportional to the point's distance from the site of initiation. These currents sum into a potential, due to the resistive nature of the tissues and fluids involved, and for simple cases, may be modelled as a simple volume conductor.

In this case, there is a function for the current at any time at any point along the fibre $I(t,x)$; given the current under the activation site $I(t,0)=I_0(t)$ and the speed with which the activation propagates, v, this is given by:

$$I(t,x)=I_0 t-x/v$$

For a linear medium, there is also a transfer function $F(x)$ from the current at any point along the fibre to the induced voltage on the measuring electrode V:

$$V(t)=\Sigma \times F(x) I(t,x)$$

With suitable scaling, it can then be seen that the measured potential from a propagating action current in a single fibre is given by the convolution of $I_0$ with F. Letting $F'(x)=F(vx)$:

$$V(t)=\Sigma \times F'(x) I_0(t-x)=F'*I_0$$

F in a simple volume conductor has a definition similar to $$F(x)=1/(d^2+x^2)$$

where d is the fibre-electrode distance, and x is the position along the fibre (relative to the electrode).

Due to the convolution equivalence, we can see that F acts as a time-domain filter kernel applied to I; and since the shape, and hence spectral characteristics, change with d, the filter will exhibit different spectral characteristics at different distances. This recognition can be exploited by, for example, picking two frequencies which are prominent in the compound action potential. By examining the ratio of the selected frequencies, changes in electrode-to-cord distance can be measured, regardless of recruitment percentage.

One key benefit of adjusting programming parameters on the basis of neural response measurements is the ability to understand the relative position of the therapeutic stimulus in the amplitude growth curve. There are two distinct tasks required in the adjustment of program parameters for spinal cord stimulation systems and these are:
1) Matching location of paraesthesia to pain location, and
2) Achieving sufficient coverage such that the area of paraesthesia overlaps the area of pain.

Both these need to be achieved without side effects.

Figure 18:
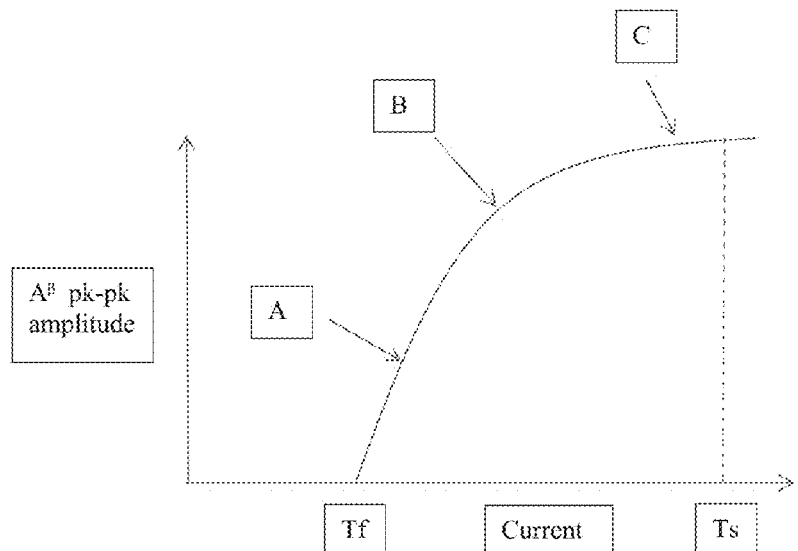
FIG. 18 is an idealised representation of an SCP amplitude growth curve to illustrate salient features.

FIG. 18 is a schematic representation of an SCP amplitude growth curve, with salient features noted. Very often a clinician will find the best electrodes for location (step (1) above) and then wind up the current to achieve the coverage desired (step (2)). In the absence of ERT measures, it is impossible for the clinician to know where the therapeutic setting is with respect to the fast response stimulus threshold (Tf in FIG. 18) and slow response stimulus threshold (Ts).

A situation where the therapeutic level is adjusted to position C in FIG. 18 is undesirable because the stimulus is close to the slow response threshold. The ideal location for the therapeutic stimulus current is at position B as this gives the most sensitive response to stimulus. Adjustments to the stimulus have a greater impact on the peripheral response from the individual. The problem then becomes ensuring that, for a stimulus of a level B, there is sufficient coverage by the paraesthesia to correspond to the area of pain.

An alternative way to address this is by stimulating at alternating locations. The choice to begin to spread the stimulus locations is based on the position of the stimulus current in the amplitude growth curve. A rule set can be developed to make those choices in an automated manner based on the neural response measurements. For instance, stimulation may be applied on alternating electrodes after the current reaches a point B.

Collection of programming data, paraesthesia coverage and neural response measurements can be used to derive a set of rules for an expert system to set up the ideal parameters for the system. Alternating or roving stimuli can be used to extend the coverage of paraesthesia. Alternating stimuli can be used with all stimuli output at the optimal rate (for example 40 Hz).

An alternative measure of the patient's posture (e.g angle detection via a triaxial accelerometer) may be used to select the slow response threshold. Alternatively, an algorithm may be implemented in the implant which simply looks for the presence of a slow response and reduces the output of the stimulator should a slow response be detected.

Another embodiment provides for measurement of a stimulation threshold and creation of a percept body map. The stimulation threshold for neural recruitment can be determined from the peak to peak amplitudes of the fast response. It corresponds to the minimum stimulation level required to produce a psycho-physical sensation. One difficulty faced in programming any neuromodulation system is to determine the locus of stimulation on a perceptual body map. This is because, in existing systems, there is no way to standardise the stimulus such that it produces a constant level of recruitment. Varying the stimulus amplitude has an effect on both the locus of the perceived stimulation and on the area covered. Stimulating at fixed point above threshold ($n \cdot T_e$) for the Aβ fibres allows stimulation at fixed level of recruitment. An accurate body map relating percept with electrode stimulation location can be determined by stimulating each electrode in turn and asking the patient to locate the locus of perception on a graphical body map. The thresholds can be determined for single electrodes as stimulating sites, or for two electrodes used in parallel as a single site, or any other applicable combination of electrodes.

A body map based on threshold or other constant recruitment condition is a useful reference for device control, as it provides a method to select electrodes to achieve the desired level of coverage. The percept body map may contribute to definition of, or constitute a portion of, the therapy map.

Currently, the task of a clinician programming such a system is to optimise the pain relief by selecting stimulus parameters and location to achieve coverage, i.e. matching the area of paraesthesia with the area over which the patient experiences pain. The choice between stimulating at one or two locations can have an impact on the power consumption of the system. Mapping the percepts at constant Aβ evoked responses allows the clinician and user to quickly identify electrodes which are aligned with the regions required for pain relief. The differences in percept for different combinations of electrodes provide a guide for lowering power consumption. For example, where two electrodes correspond to the same paraesthesia location, then stimulation on those two together will reduce the power consumption of the device.

Yet another embodiment provides for stimulation below the threshold at which paraesthesia is perceived. There are a number of therapeutic benefits obtainable from spinal cord stimulation. For example spinal cord stimulation has been used to treat chronic peripheral vascular disease, in which the mode of action appears to be stimulation of the sympathetic nervous system. Spinal cord stimulation has also been found to be effective in the treatment of chronic leg ulcers. The control of stimulus parameters is complex in this clinical condition. The clinician is not necessarily aiming to produce a paraesthesia in order to generate clinically therapeutic stimulation of the sympathetic nerves. However, in conventional SCS systems, the only indicator that stimulus parameters are producing neuronal depolarisations is through the patient reporting the presence of a paraesthesia. The present embodiment, using neural response measurements, provides a method to objectively quantify the stimulation threshold and may thus permit effective use of sub-threshold stimuli. Using this threshold and its potential variations due to posture, a stimulus parameter can be selected which is below psychophysical threshold, so that continual excitation can be achieved which is below sensation threshold, and independent of posture.

Figure 9:
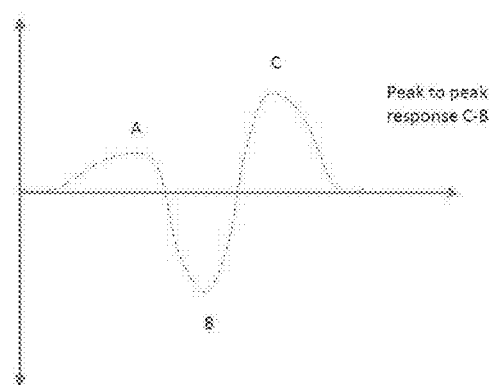
FIG. 9 is a schematic diagram illustrating the measurement of the peak to peak amplitude of the evoked neural response.

In another embodiment, the fast response is measured to set the comfort level without reference to the slow response and indeed possibly without ever causing a slow response. The recorded electrically evoked compound action potential is the sum of a multitude of single fibre evoked responses, and its strength represents the level of recruitment of the fibres (i.e. the size of the signal is proportional to the number of fibres responding to the stimulus). A convenient way to represent this is to measure the peak to peak amplitude of the response (C-B in FIG. 9).

Figure 10:
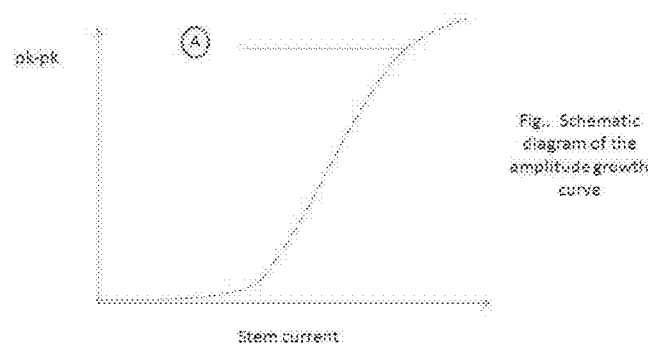
FIG. 10 is a schematic diagram of the neural response amplitude growth curve relative to stimulus current.

The amplitude growth curve for the peak to, peak response is readily obtained by measuring the responses at different stimulus parameters (pulse width and current level). The charge on the electrode generates equivalent responses independent of the pulse width. The fast response amplitude growth curve, as illustrated in FIG. 10, can be used to set the comfort level (the level beyond which unwanted side effect stimuli would result), simply by inspection of the growth curve. This embodiment may thus avoid the need to deliberately induce a slow response in order to ascertain the comfort threshold. The stimulus needs to be maintained around or below the point A indicated in FIG. 10. Increasing the current above this point results in no further desirable recruitment and it potentially results in a generation of unwanted or unpleasant slow responses. Point A may be estimated from the amplitude measurements by finding an inflection point in the growth curve, or by noting a reducing gradient of the curve, for example.

Electrode to electrode variation in stimulus thresholds may indicate differences in proximity of electrode to the spinal cord, or that the electrode may be adjacent to neural regions of greater sensitivity. The procedure to locate the ideal electrodes for stimulation efficiency is to create an electrode sensitivity map. This is obtained simply by performing a stimulus current sweep on each electrode, while obtaining neural response measurements at each level, so as to obtain the evoked response amplitude vs. stimulus current curve, for all stimulating sites. The electrode sensitivity map may then contribute to definition of, or constitute a portion of, the therapy map.

Further embodiments of the invention provide for estimation of the spinal cord-to-electrode distance. In order to maintain a constant level of recruitment, it is necessary to estimate the evoked neural response level arising from a particular stimulation. Given that one of the primary factors affecting recruitment efficacy is relative motion between the spinal cord and the electrodes, it is extremely useful to estimate the cord-electrode distance.

In another embodiment for estimating the cord-to-electrode distance, the relationship of the evoked SCP to the stimulation is exploited. For simple stimulation in the linear region of the amplitude growth curve, recruitment varies with the number of fibres for which the activating function (the axial second derivative of voltage) is above threshold. It can be shown that, in a homogeneous volume conductor (HVC), the activating function varies with $1/d^2$. Hence, for a fixed stimulus current in a HVC, the recruitment varies approximately with $1/d^2$. This embodiment also recognises that, in measuring the SCP, two distance-related factors are prominent. Due to the nature of the fibre, having discrete nodes of Ranvier easily modelled as a line of point current sources, the SCP amplitude in a HVC varies with $1/d^2$ (as well as with fibre diameter). This means that in the linear region of the amplitude growth curve, the combined effect of recruitment sensitivity to d and measurement sensitivity to d causes the measured SCP amplitude to approximately vary with current$*1/d^2*1/d^2$, or current/$d^4$. Based on this recognition, this embodiment therefore applies an algorithm which uses probe stimuli in the linear range (between threshold and onset of saturation), to estimate the cord distance relative to some calibration value. Hence, the recruitment can be estimated for a particular stimulus, relative to some calibration point.

In another embodiment of the invention lateral movement of an electrode is monitored and estimated. This embodiment recognises that anecdotal data from sheep experiments, as well as a consideration of spinal cord anatomy, suggests that as the epidural stimulation site shifts laterally from the midline, the chance of eliciting motor reflexes and other responses of the motor neurons increases. For a given stimulus intensity, if the slow responses appear or become larger than previously, this is an indicator that lateral movement of the electrode has occurred. This scenario may lead to undesired sensation and may need to be rectified. In such embodiments a paddle electrode may be used, comprising multiple columns of electrodes, and then the selection of stimulation electrodes may be changed such that the new stimulus electrodes are medial of the previous off-centre stimulating electrodes. If a single "percutaneous" electrode array is used, the stimulus intensity may be reduced to avoid the undesired sensation produced, or again the stimulus location may be shifted.

Embodiments of the invention may be applied only occasionally, for example only in a clinical setting. Alternatively, automated neural response measurements in accordance with the various embodiments of the invention may be used regularly, or even substantially continuously to adjust the system in real time.

Yet another embodiment of the invention may obtain measures of both the neural response and also electrode impedance as measures of activity for adjustment of the system. The evoked response measurements are sensitive to the distance between the excited neural tissue and the sense electrode. Variations in the position of the electrode affect both the level of recruitment and also the strength of the measured evoked response due to the losses of the electric field propagating in the medium. The variation in the evoked response which is induced by relative movement of the electrode and spinal cord can be used to detect activity and movement of the recipient.

Many recipients of spinal neuromodulators report discomfort or changes in modulation with movement. The evoked potential change could be used to control the stimulus current in a "tight" feedback loop or in a "loose" feedback loop, in order to avoid the stimulus from causing discomfort when the user moves or changes posture. In a loose feedback loop, the evoked response could be used to control the stimulus between say two values, a first setting used for ambulatory periods or periods of activity, and a second setting used for periods with relatively stable evoked response measures. A useful example may be the detection of periods of sleep (relatively low movement) where it would be desirable to turn down the amount of stimulation to conserve battery life during periods of rest. Alternatively, during periods of high activity it may be preferable for the implantee to receive a lower therapeutic (or no therapeutic stimulation) to lower the likelihood of unwanted undesirable stimulation.

In this embodiment, changes in movement are detected and the pattern of these changes is used to control device parameters. In addition to adjusting the stimulus level, this embodiment adjusts other device parameters which have an impact on the operation of the system. Noting that continuous recording of the evoked potential consumes additional electrical power, this embodiment further controls the rate at which measurements are obtained in response to the level of activity. The level of implantee activity may also be logged by the system and used as a measure of the performance of the system in achieving pain relief.

Figure 11:
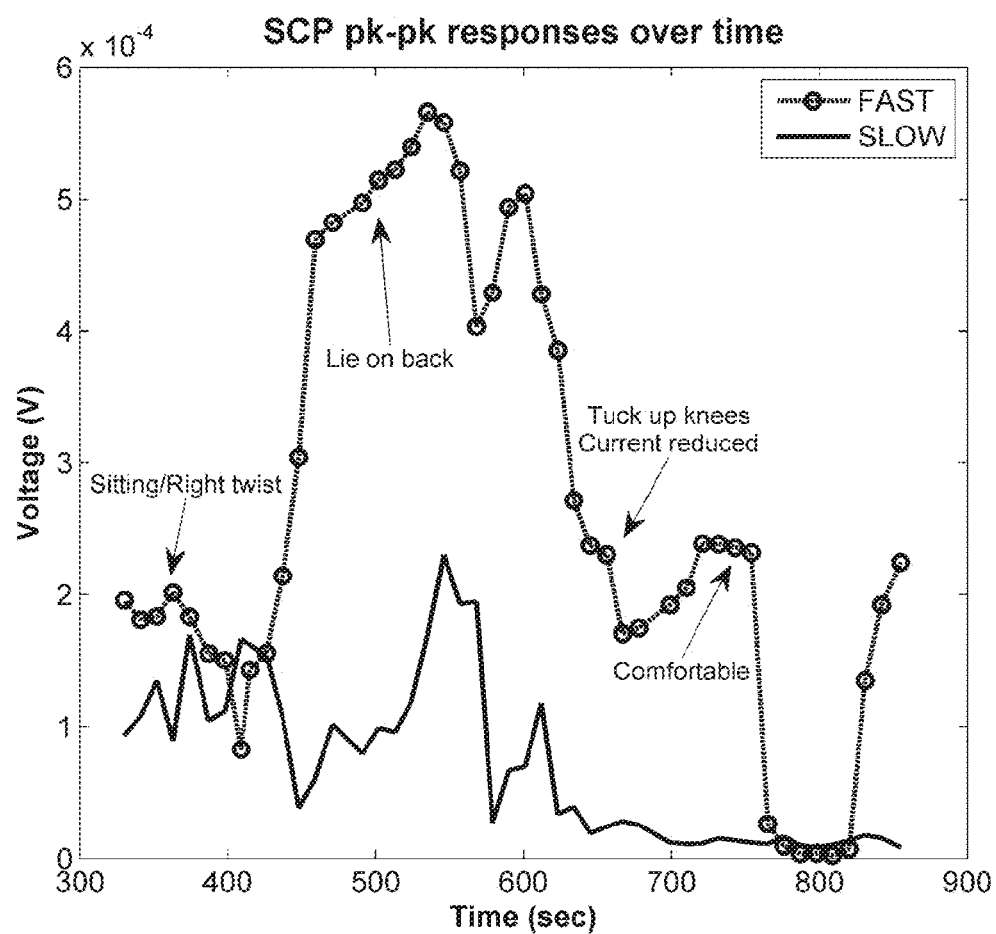
FIG. 11 plots the amplitude of the "fast" and "slow" responses in a human subject while performing postural manipulations.

In embodiments addressing postural changes, a further issue arises in that gross posture alone (as might be measured by an implanted accelerometer) may not sufficiently indicate the appropriate parameters. FIG. 11 provides plots of the amplitude of the "fast" and "slow" responses in a human subject while performing postural manipulations. The posture or relative position of the stimulator gives information about the position of the stimulator. However, in the "fast" curve of FIG. 11 the stimulation efficiency changed when the patient was lying on their back and asked to bring their knees to their chest. Although the stimulation efficiency and patient's perception change significantly, an implanted accelerometer would not have been able to sense these postural changes because the device remains at the same orientation. In contrast, neural response measurements can be used to greatly improve the effectiveness of neurostimulator adjustment when combined with accelerometer measurements of posture. Simultaneously recording neural responses and measuring posture with an accelerometer can be used in an automated process to determine the appropriate parameters for the neurostimulator for a wide range of postures. Notably, such simultaneous recording does not necessarily require implantation of a device equipped with neural response recording capabilities, as it can be performed during the trial stimulation phase when patients have been implanted with an externalised lead.

In such embodiments utilising simultaneous neural response measurements and accelerometer posture measurements, determining the patient parameters comprises:
1. the neural response measurement system is used to record responses under an initially programmed set of conditions.
2. The patient changes posture and the posture is measured via accelerometer and responses recorded at the new posture.
3. Adjustments are made to the stimulus parameters based on the evoked response measurements. The adjustments are made to bring the neural response measure equal to the first neural response measure, preferably accounting for varying measurement sensitivity arising from a changed electrode-to-fibre distance d. Note that the adjustments can be done automatically in a feedback loop.
4. A table of program parameters versus posture parameters is updated with new posture data and program data determined from the neural response.

The process outlined can use any or all of the feedback techniques described herein to adjust the stimulation parameters automatically. In this way programming of the device for different posture settings is simply a matter of setting up the process as described and asking the patient to vary their posture. This could be done over days, for example during the trial stimulation period, improving data quality. An indicator could be provided to give feedback to the patient on the percentage of possible posture variations as determined by the range of the measurement device.

Another advantage of the system as described is the ability to identify postures for which there are ambiguous stimulation parameters; for example, supine with straight legs versus supine with knees to chest. Continuous recording of both posture and feedback parameters based on neural response measurements may allow identification of posture values for which there are two or more different stimulation parameters. If used without neural response measurements, the patient parameter set chosen from an ambiguous parameter set could be the set corresponding to the lowest stimulation current, thus preventing unwanted side effects.

Neural response measurements conducted during a trial stimulation period may be used to create a table of parameters for use with accelerometer-based implants. Neural response measurements can also be used continuously with accelerometer-based measurement. An accelerometer or simple passive movement detection could be used as an indicator of activity. Neural response measurements consume power and so the rate at which they are obtained will have an impact on the battery life of the system. It is highly desirable to manage the rate of measurement (and hence the power consumption). An accelerometer or passive movement detector could be used to detect movement of any type, in response to which the neural response measurement sample rate may be adjusted up or down, so that the response is optimally adjusted with the minimum number of neural response samples acquired.

Employing neural response measurement in a neuromodulation system leads to a variety of available mechanisms for improving the therapeutic outcome of SCS implantees. Discussed below are various control algorithms based on neural response feedback signals. It should be noted that all of these feedback mechanisms may be enabled only when movement is detected, since this is when the stimulus needs to be updated to optimise the pain relief. Enabling feedback control only when movement is detected may also lower the overall power consumption of the implant. Detection of movement may be achieved in a number of ways, including: monitoring via ball-in-tube type detectors, accelerometers, gyroscopes, etc.

In order to maintain a constant level of analgesia, it is desirable to recruit enough of the appropriate dorsal column fibres, while avoiding recruitment at levels or in areas associated with side effects. Control of recruitment can be achieved by varying any one of several parameters, such as current or pulse-width. However, when modulating a single parameter, patient discomfort can limit the range of conditions under which recruitment can be held constant. For example, as current increases, fibres lateral to the electrode are more likely to be recruited. Thus, instead of controlling one parameter at a time, it is possible to control several. The choice of parameters is made to minimise discomfort and stimulation energy for any desired stimulation command (up to some programmed limit). FIG. 12 is a schematic of such a feedback controller based on recruitment of neurons.

The simplest implementation is a piecewise specification of stimulation parameters from the command. For example, we may specify that the injected charge should be proportional to the command value C. The Command generated is a value which is proportional to the error in the recorded response (ie the difference between the set point and the measured response). The parameter selector can select any parameter to adjust (pulse width, current level, frequency of burst etc). One simple option is to make the charge delivered proportional to the command value which reduces the feedback loop to a simple proportional control loop.

The optimal command-to-stimulus mapping depends on factors including spinal geometry, control loop parameters and desired performance, and the psychophysical requirements of the individual patient. Thus it may be necessary to select between different parameter-selection algorithms depending on external factors, such as movement detection or patient controls.

Referring again to FIG. 13, this reveals an opportunity for defining an algorithm which is based on the presence or absence of $A\beta$ and slow responses, as follows:
1. A stimulus Sp ($=Tf+\Delta Ts$) targeted to be less than the therapeutic stimulus but greater than threshold Tf is used to evoke a response.
   a. If a response is detected in <2.0 ms then do nothing else.
   b. If no response is detected, increment the threshold Tf by an increment $\Delta Ts$
2. A stimulus SL ($=Ts-\Delta Ts$) targeted to be greater than the therapeutic stimulus but less than that required to elicit a slow response is output
   a. If a slow response is detected, decrement the threshold Ts by $\Delta Ts$
   b. If a slow response is not detected, then do nothing.
3. The therapy setting is calculated as a ratio of the difference between the thresholds Tf and Ts.

Figure 3:
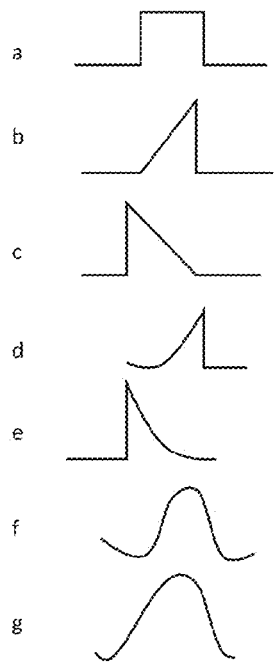
FIG. 3 illustrates a selection of pulse shapes which may be tested to determine the most efficient at producing depolarisation.

Moreover, the present invention recognises that non-rectangular pulses have an effect on the strength-duration relationships of recruitment. FIG. 3 illustrates a selection of the many different possible stimulus pulse shapes which may be tested to determine which is most efficient at producing depolarisation. The strength-duration curve relates the time for which a stimulus is applied to the nerve, to the recruitment level of the fibres in the nerve. The temporal recruitment responses for different fibres of different sizes depend on the pulse shape. A large number of large diameter fibres are recruited at the beginning of a square pulse (FIG. 3a), and an approximately constant uniform number of small fibres are then recruited over time as the pulse continues. In contrast, negative sloping waveforms (FIGS. 3c, 3e) recruit high numbers of both large and small diameter fibres. The adjustment of stimulation parameters for a spinal cord stimulator requires recruitment of $A\beta$ fibres. Recruiting smaller fibres such as $A\delta$ fibres may cause undesirable side effects.

If there is a wide range of different fibre diameters being recruited then the $(N_1^t-P_2^t)$ will spread out as the action potential propagates up the spinal cord. This is because as disparate fibre classes are recruited, the P-N-P morphology of the CAP is replaced by a more complicated waveform, which can generally be thought of as equivalent to the summation of one P-N-P wave per fibre class.

There are thus a number of salient parameters which may be focussed upon, including the strength (amplitude) of the evoked response, which relates to the recruitment, and the evoked response dispersion which relates to the selectivity of fibre classes.

The present invention recognises that there are a number of ways to adjust the stimulus parameters (such as stimulus shape and amplitude) in order to optimise the selectivity and efficiency of recruitment. However, the past approach of optimising a stimulus on the basis of patient feedback is entirely impractical when the parameter search space is made so large as to include pulse shape, amplitude, interphase gap, and so on. Accordingly, to search for an optimally efficient set of stimulus pulse parameters, the present embodiment provides for automated optimisation of the stimulus pulse parameters based on measurement of the evoked response arising from test stimuli having varied stimulus parameters. The stimulus optimisation process in this embodiment occurs automatically, and may be completed within minutes and therefore performed regularly, as opposed to clinical optimisation.

There are a number of ways to adjust the stimulus parameters. In the present embodiment, the stimulus parameter search space is explored by iteratively applying stimuli and obtaining measurements of neural responses thereto, assessing how well the measured response confirms to a desired response, and refining the stimulus parameters in accordance with a genetic, heuristic or other search algorithm. A genetic algorithm, for example, may separate the parameter set into two sets of traits, and iteratively modify the contents of each set, whereby each iteration combines the traits of the more successful parameter values to form a new set of parameters for stimulus application.

Figure 4:
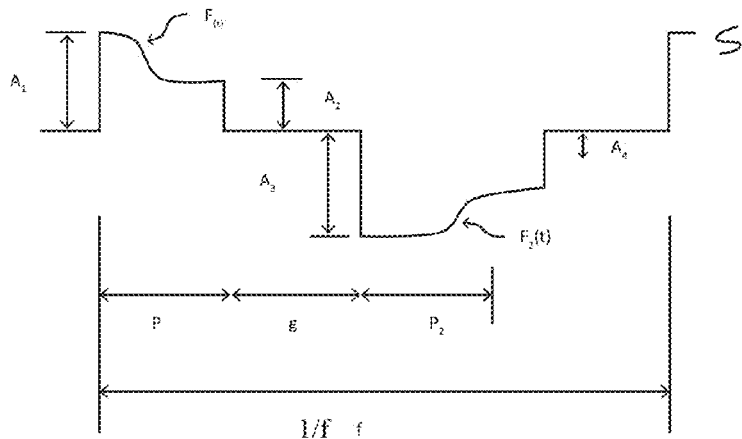
FIG. 4 illustrates a set of stimulus parameters which may be controlled in accordance with the present invention.

The present embodiment thus permits a considerably more generalised definition of the stimulus, as shown in FIG. 4. In this embodiment, parameters which are varied within the parameter search space include:

| | |
|---|---|
| Amplitude | $A_1, A_2, A_3, A_4$ which are the amplitudes of the various peaks. |
| Pulse period | $P_1, P_2$ the duration of the pulses. |
| Interpulse gap | g the gap between the first pulse and the second pulse. |
| Pulse function | $F_1(t)$ and $F_2(t)$ define the shape of each phase |
| Frequency | f determines the repetition rate for the stimulus |

For example, a pure sinusoidal response can be generated with f(t) as a sin function g=0, A2=A3=0. A conventional square biphasic pulse has a parameter set $F_1(t)=-F_2(t)=$ A1=A2=−A3=−A4.

FIG. 5 illustrates measured ovine compound action potentials, which arose in response to successively applied stimuli of varying amplitudes, in order to ascertain suitable threshold and comfort levels. The stimulus pulse width was 40 μs. FIG. 5 illustrates that stimulus pulse amplitude can be progressively varied in order to determine a stimulus amplitude at which the greatest fast response is evoked, with the least slow response.

By iteratively refining the stimulus parameters and applying differing stimuli under control of a suitable search algorithm e.g. a genetic algorithm, the stimulus parameter search space can be effectively and swiftly explored to identify a specific set of values for the stimulus parameters which best generate a desired evoked response. There are several parameters that are useful to optimise for the individual. The total charge delivered per stimulus pulse determines the power consumption of the device and hence the time between recharges for a rechargeable device or the lifetime of the device for a non-rechargeable device. The pulse parameters, duration of the interphase gap etc, can be varied and the combination which delivers the desired evoked response for the minimum delivered charge can be determined by application of a suitable search technique.

It will be appreciated by persons skilled in the art that numerous variations and/or modifications may be made to the invention as shown in the specific embodiments without departing from the spirit or scope of the invention as broadly described. For example, embodiments described in the context of spinal cord stimulation may in some cases be applied to other forms of neural stimulation and it is to be understood that such other contexts are within the scope of the present invention. Further, in alternative embodiments the neural response measurement may be conducted in accordance with any suitable CAP measurement technique. The present embodiments are, therefore, to be considered in all respects as illustrative and not restrictive.

The invention claimed is:

1. An automated method of controlling a neural stimulus, the method comprising:
   applying the neural stimulus to a neural pathway in order to give rise to an evoked action potential on the neural pathway, the stimulus being applied as defined by a set of parameter values;
   measuring a neural compound action potential response evoked by the stimulus and deriving from the measured evoked response a feedback variable;
   comparing the feedback variable to a therapy map, the therapy map defining a therapeutic relationship of control variable to feedback variable, and determining from the therapy map a required change in the control variable in order to improve alignment of the feedback variable with the therapy map;
   altering one or more of the stimulus parameter values to effect the required change in the control variable; and
   iteratively performing the applying, measuring, comparing and altering, in order to improve alignment of the feedback variable with the therapy map over time;
   wherein the feedback variable is a type of measure of evoked response strength, and the control variable is a type of stimulus intensity, and the therapeutic relationship represents a locus defining a desired output measure of evoked response strength for a given input stimulus intensity, with the desired output measure of evoked response strength being defined in a manner which varies for varying stimulus intensity.

2. The method of claim 1 wherein the therapy map defines the therapeutic relationship of control variable to feedback variable in a manner which is adaptive in response to changed recruitment sensitivity and/or measurement sensitivity.

3. The method of claim 1 wherein the locus comprises a discontinuous stepped locus.

4. The method of claim 3 wherein a hysteresis is effected by the therapy map defining partially overlapping steps in the discontinuous stepped locus.

5. The method of claim 1 wherein the locus comprises a continuous curve.

6. The method of claim 5 wherein the locus comprises a continuous monotonic curve.

7. The method of claim 6 wherein the locus comprises a continuous monotonic decreasing curve.

8. The method of claim 1 wherein the therapy map is fitted to a user by determining a plurality of preferred set points, and by fitting the therapy map to the set points.

9. The method of claim 8 wherein the preferred set points are determined in an automated manner from user control inputs for preferred stimulus intensity.

10. The method of claim 8 wherein the preferred set points are determined in an automated manner from automated estimations of a stimulus threshold at a given posture.

11. The method of claim 8 wherein the therapy map is derived from the preferred set points by linear interpolation between the preferred set points.

12. The method of claim 1 further providing differential slew rates whereby a rate of change of the control variable in response to a detected overstimulation condition is more rapid than a rate of change of the control variable in response to a detected understimulation condition.

13. The method of claim 1 wherein the therapy map is derived at least in part from a body percept map.

14. The method of claim 1 wherein the feedback variable is an estimate of an electrode-to-fibre distance d.

15. The method of claim 14 wherein the electrode to fibre distance d is estimated by obtaining neural response amplitude measurements in response to at least two stimuli of differing current level for constant d, the stimuli being within a linear range of a neural recruitment versus current curve, taking a linear extrapolation of neural response amplitude measurements to a point of zero neural response to estimate a stimulus current threshold, and estimating d from the stimulus current threshold.

16. The method of claim 14 wherein the estimate for d is obtained by measuring an amplitude ($R_{e1p1}$, $R_{e5p1}$) of the neural compound action potential response as measured at two spaced apart sense electrodes e1 and e5 for a first stimulus, and measuring an amplitude ($R_{e1p2}$, $R_{e5p2}$) of the neural response at the two sense electrodes for a second stimulus having the same parameters as the first stimulus after a change in d, and calculating the change in recruitment scaling factor $A_s$ in response to d as:

$$(R_{e1p2}/R_{e1p1})-(R_{e5p2}/R_{e5p1})=A_s$$

17. The method of claim 1 wherein the feedback variable comprises a measure of dispersion of the neural compound action potential response relative to distance from a stimulus site and wherein increased dispersion is taken to indicate increased electrode-to-fibre distance d.

18. An implantable device for controllably applying a neural stimulus, the device comprising:
- a plurality of electrodes including one or more nominal stimulus electrodes and one or more nominal sense electrodes;
- a stimulus source for providing a stimulus to be delivered from the one or more stimulus electrodes to a neural pathway in order to give rise to an evoked action potential on the neural pathway;
- measurement circuitry for recording a neural compound action potential signal sensed at the one or more nominal sense electrodes; and
- a control unit configured to:
    - control application of a neural stimulus as defined by a set of parameter values;
    - measure via the measurement circuitry a neural compound action potential response evoked by the stimulus;
    - determine from the measured neural compound action potential response a feedback variable;
    - compare the feedback variable to a therapy map, the therapy map defining a therapeutic relationship of control variable to feedback variable;
    - alter one or more of the stimulus parameter values to effect a required change in the control variable, and
    - iteratively perform the applying, measuring, comparing and altering, in order to improve alignment of the feedback variable with the therapy map over time;
- wherein the feedback variable is a type of measure of evoked response strength, and the control variable is a type of stimulus intensity, and the therapeutic relationship represents a locus defining a desired output measure of evoked response strength for a given input stimulus intensity, with the desired output measure of evoked response strength being defined in a manner which varies for varying stimulus intensity.

* * * * *